(12) United States Patent
Hacker et al.

(10) Patent No.: US 9,974,640 B2
(45) Date of Patent: *May 22, 2018

(54) PELVIC IMPLANT AND TREATMENT METHOD

(71) Applicant: Boston Scientific Scimed, Inc., Maple Grove, MN (US)

(72) Inventors: Dean W. Hacker, Maple Grove, MN (US); Karl A. Jagger, Deephaven, MN (US); Benjamin M. Wilke, Minneapolis, MN (US); Seth C. Kelto, Minneapolis, MN (US); Jessica E. Felton, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 223 days.

This patent is subject to a terminal disclaimer.

(21) Appl. No.: 14/346,383

(22) PCT Filed: Sep. 24, 2012

(86) PCT No.: PCT/US2012/056905
§ 371 (c)(1),
(2) Date: Mar. 21, 2014

(87) PCT Pub. No.: WO2013/044228
PCT Pub. Date: Mar. 28, 2013

(65) Prior Publication Data
US 2014/0257032 A1    Sep. 11, 2014

Related U.S. Application Data

(60) Provisional application No. 61/537,631, filed on Sep. 22, 2011, provisional application No. 61/558,271, (Continued)

(51) Int. Cl.
*A61F 2/00* (2006.01)
*A61B 17/04* (2006.01)
(Continued)

(52) U.S. Cl.
CPC ........ *A61F 2/0063* (2013.01); *A61B 17/0401* (2013.01); *A61B 17/0625* (2013.01);
(Continued)

(58) Field of Classification Search
CPC .... A61F 2/0004; A61F 2/0031; A61F 2/0045; A61F 2/0063; A61F 2/0077; A61F 2002/0068; A61F 2002/0081
(Continued)

(56) References Cited

U.S. PATENT DOCUMENTS 4,440,526 A * 4/1984 Koppers ............. E21D 21/0093
405/259.5
5,520,606 A      5/1996 Schoolman et al.
(Continued)

FOREIGN PATENT DOCUMENTS

EP    1937183 A1    7/2008
EP    1539044 B1    4/2011
(Continued)

OTHER PUBLICATIONS

International Search Report rendered by the International Searching Authority dated Dec. 3, 2012 for PCT Application No. PCT/US2012/056905, 2 Pages.
(Continued)

*Primary Examiner* — John Lacyk
(74) *Attorney, Agent, or Firm* — Brake Hughes Bellermann LLP

(57) ABSTRACT

A unitary or homogeneous patterned implant is provided. The implant is constructed of patterned cells formed by way of a molding, die casting, laser etching, laser cutting, extrud-
(Continued)

ing, and the like. Portions of the implant can be formed into sinusoid or other waveform strut members. One or more undulating anchor arms or rods extend out from the implant for tissue fixation, with the one or more undulating anchor arms including one or more arcuate bends.

25 Claims, 24 Drawing Sheets

Related U.S. Application Data filed on Nov. 10, 2011, provisional application No. 61/547,475, filed on Oct. 14, 2011, provisional application No. 61/546,877, filed on Oct. 13, 2011.

(51) Int. Cl.
*A61B 17/06* (2006.01)
*A61B 17/062* (2006.01)
*A61B 5/107* (2006.01)
*A61B 17/00* (2006.01)

(52) U.S. Cl.
CPC ...... *A61B 17/06109* (2013.01); *A61F 2/0045* (2013.01); *A61B 5/107* (2013.01); *A61B 2017/00805* (2013.01); *A61B 2017/0412* (2013.01); *A61B 2017/0414* (2013.01); *A61B 2017/0427* (2013.01); *A61B 2017/0445* (2013.01); *A61B 2017/0446* (2013.01); *A61B 2017/06176* (2013.01); *A61F 2002/0068* (2013.01); *A61F 2002/0072* (2013.01); *A61F 2240/004* (2013.01); *A61F 2250/0097* (2013.01)

(58) Field of Classification Search
USPC .................. 600/29–32, 37; 606/151, 153
See application file for complete search history.

(56) References Cited

U.S. PATENT DOCUMENTS

| | | | |
|---|---|---|---|
| 5,824,050 A | 10/1998 | Karwoski et al. |
| 5,997,554 A | 12/1999 | Thompson |
| 6,010,447 A | 1/2000 | Kardjian |
| 6,042,666 A | 3/2000 | Karwoski et al. |
| 6,066,776 A | 5/2000 | Goodwin et al. |
| 6,231,598 B1 | 5/2001 | Berry et al. |
| 6,464,720 B2 | 10/2002 | Boatman et al. |
| 6,652,450 B2 | 11/2003 | Neisz et al. |
| 7,083,568 B2 | 8/2006 | Neisz et al. |
| 7,105,018 B1 | 9/2006 | Yip et al. |
| 7,413,574 B2 | 8/2008 | Yip et al. |
| 7,416,558 B2 | 8/2008 | Yip et al. |
| 8,709,096 B2 | 4/2014 | Gingras et al. |
| 8,796,015 B2 | 8/2014 | Gingras |
| 9,414,903 B2 | 8/2016 | Allen et al. |
| 9,440,007 B2 | 9/2016 | Gingras et al. |
| 2001/0027339 A1 | 10/2001 | Boatman et al. |
| 2002/0091438 A1 | 7/2002 | Trozera |
| 2002/0143234 A1 | 10/2002 | Lovuolo |
| 2004/0054253 A1 | 3/2004 | Snitkin et al. |
| 2004/0059356 A1 | 3/2004 | Gingras |
| 2004/0106847 A1 | 6/2004 | Benderev |
| 2004/0260381 A1* | 12/2004 | Marco ............... A61F 2/95 623/1.11 |
| 2005/0149169 A1 | 7/2005 | Wang et al. |
| 2005/0234291 A1 | 10/2005 | Gingras |
| 2005/0240076 A1 | 10/2005 | Neisz et al. |
| 2005/0288769 A1 | 12/2005 | Globerman |
| 2006/0089525 A1 | 4/2006 | Mamo et al. |
| 2006/0106419 A1 | 5/2006 | Gingras |
| 2006/0141012 A1 | 6/2006 | Gingras |
| 2006/0195010 A1 | 8/2006 | Arnal et al. |
| 2007/0154515 A1 | 7/2007 | Johnson et al. |
| 2007/0173864 A1 | 7/2007 | Chu et al. |
| 2007/0282160 A1 | 12/2007 | Sheu et al. |
| 2007/0293930 A1 | 12/2007 | Wang et al. |
| 2008/0076963 A1 | 3/2008 | Goria et al. |
| 2008/0178459 A1 | 7/2008 | Barr et al. |
| 2008/0255655 A1 | 10/2008 | Kusleika et al. |
| 2008/0269748 A1 | 10/2008 | Justin et al. |
| 2008/0279911 A1 | 11/2008 | Sutermeister et al. |
| 2009/0041978 A1 | 2/2009 | Sogard et al. |
| 2009/0099409 A1 | 4/2009 | Luehrs et al. |
| 2009/0117334 A1 | 5/2009 | Sogard et al. |
| 2009/0171465 A1 | 7/2009 | Bucay-Couto et al. |
| 2009/0192346 A1 | 7/2009 | Rosenblatt |
| 2009/0216338 A1 | 8/2009 | Gingras et al. |
| 2009/0222025 A1 | 9/2009 | Catanese, III et al. |
| 2010/0082113 A1 | 4/2010 | Gingras et al. |
| 2010/0113868 A1 | 5/2010 | Goldman |
| 2010/0131045 A1 | 5/2010 | Globerman et al. |
| 2010/0174134 A1 | 7/2010 | Anderson et al. |
| 2010/0197999 A1 | 8/2010 | Deegan et al. |
| 2010/0210897 A1 | 8/2010 | Arnal et al. |
| 2010/0305695 A1 | 12/2010 | Devonec |
| 2010/0331612 A1 | 12/2010 | Lashinski et al. |
| 2011/0004290 A1 | 1/2011 | Bales, Jr. et al. |
| 2011/0082328 A1 | 4/2011 | Gozzi et al. |
| 2011/0082481 A1 | 4/2011 | Gingras et al. |
| 2011/0124956 A1 | 5/2011 | Mujwid et al. |
| 2011/0144417 A1* | 6/2011 | Jagger ............... A61F 2/0045 600/30 |
| 2013/0204075 A1 | 8/2013 | Allen et al. |
| 2014/0100590 A1 | 4/2014 | Gingras et al. |
| 2014/0178997 A1 | 6/2014 | Gingras |
| 2014/0257032 A1 | 9/2014 | Hacker et al. |
| 2014/0374004 A1 | 12/2014 | Gingras |
| 2017/0105829 A1 | 4/2017 | Hacker et al. |

FOREIGN PATENT DOCUMENTS

| | | |
|---|---|---|
| WO | 2001080774 A1 | 11/2001 |
| WO | 2004017869 A1 | 3/2004 |
| WO | 2005094741 A1 | 10/2005 |
| WO | 2006108145 A1 | 10/2006 |
| WO | 2007149348 A2 | 12/2007 |
| WO | 2008097592 A2 | 8/2008 |
| WO | 2013016306 A1 | 1/2013 |

OTHER PUBLICATIONS

Extended European Search Report dated Oct. 4, 2015 for PCT Application No. PCT/US2012/056905, 5 Pages.
International Written Opinion rendered by the International Searching Authority dated Dec. 3, 2012 for PCT Application No. PCT/US2012/056905, 6 Pages.
Third Examiner Report for Australian Application No. 2012312022, dated Feb. 17, 2017, 4 pages.
Notice of Acceptance for Australian Application No. 2012312022, dated Apr. 7, 2017, 4 pages.
Third Examiner Report for Australian Application No. 20121312022, dated Feb. 17, 2017, 4 pages.

* cited by examiner

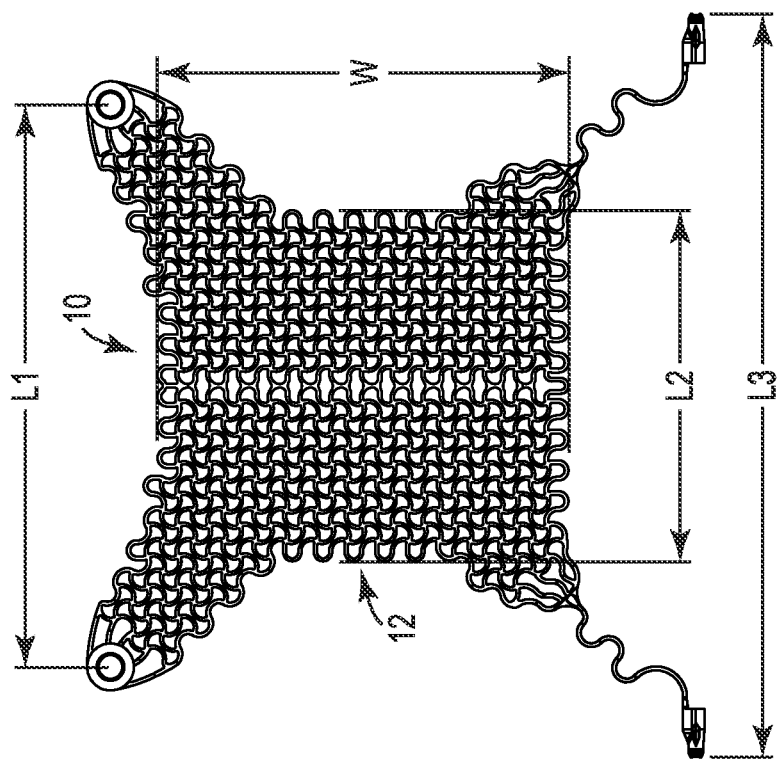
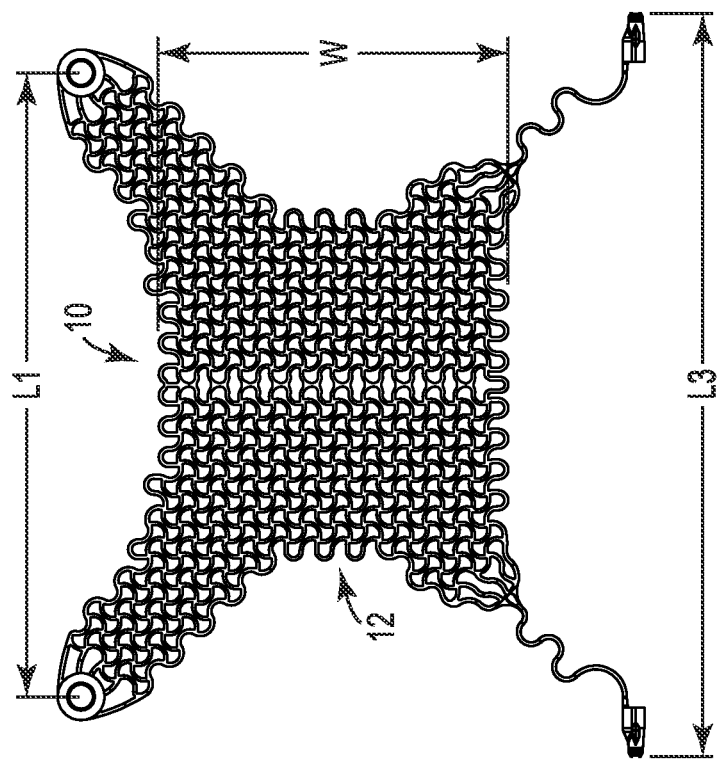

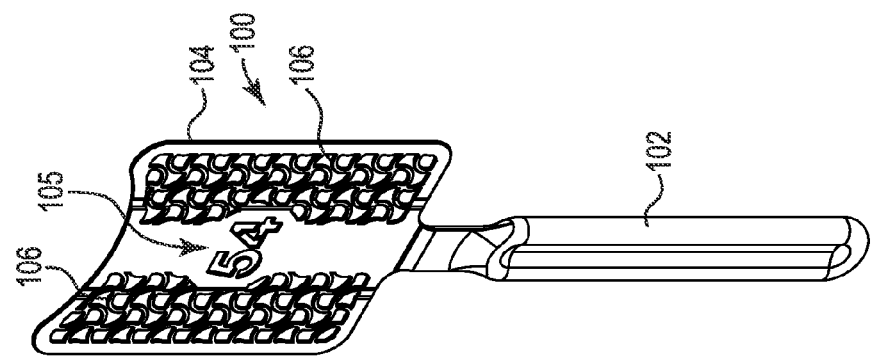
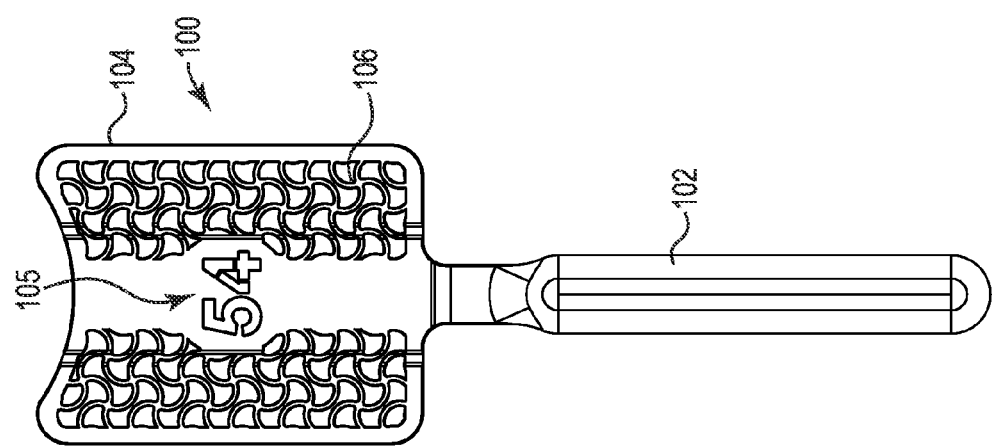

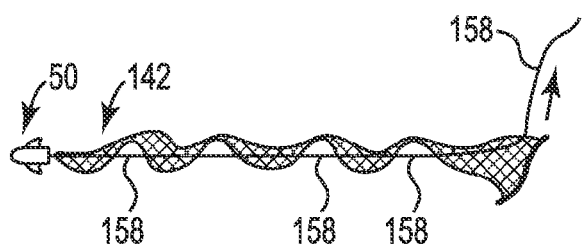
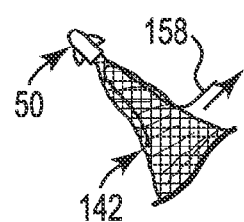
Fig. 40      Fig. 41
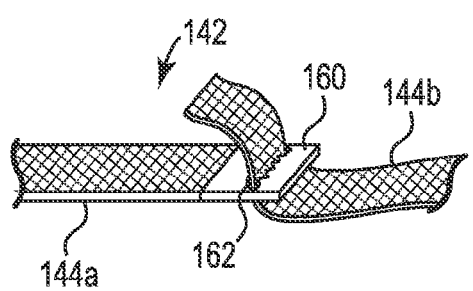
Fig. 42
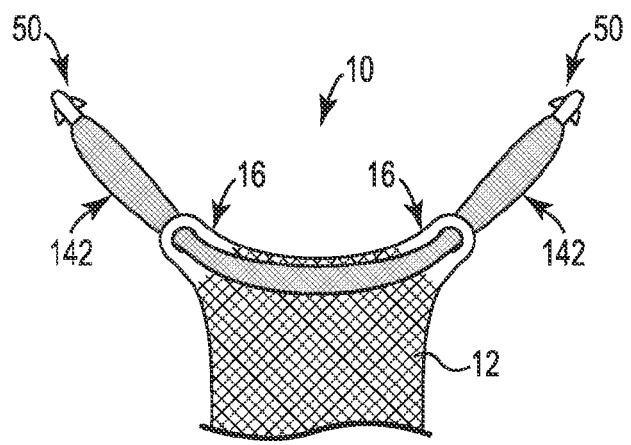
Fig. 43

PELVIC IMPLANT AND TREATMENT METHOD

PRIORITY

This Application claims priority to and the benefit of U.S. Provisional Patent Application No. 61/537,631, filed Sep. 22, 2011, U.S. Provisional Patent Application No. 61/546,877, filed Oct. 13, 2011, U.S. Provisional Patent Application No. 61/547,475, filed Oct. 14, 2011, and U.S. Provisional Patent Application No. 61/558,271, filed Nov. 10, 2011; which are all fully incorporated herein by reference in their entireties.

FIELD OF THE INVENTION

The present invention relates generally to surgical methods and apparatus and, more specifically, to surgically implantable patterned support devices and methods for forming and using the same.

BACKGROUND OF THE INVENTION

Pelvic health for men and women is a medical area of increasing importance, at least in part due to an aging population. Examples of common pelvic ailments include incontinence (fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed. Physical stresses that can cause urinary incontinence include jumping, coughing, sneezing and laughing to name a few.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Many strategies have been implemented over the years to provide mesh implants adapted to enhance therapeutic support of the respective pelvic tissues. For instance, sling and other implant devices are known to provide support of the urethra or bladder neck in treating urinary incontinence in patients. Further, various mesh implants have been adapted to provide pelvic floor support to treat certain prolapse disorders.

Many of the implants promoted for treating incontinence, prolapse and other pelvic disorders were born from and inherited the material and geometric restraints of existing stent and hernia implants. While objectively effective in their respective applications, such stent and hernia implants are naturally constructed to address very different issues. Namely, the requisite barrier, rigidity and tissue integration and compatibility needs of a hernia mesh or vascular stent implant can be very disparate from the implant characteristics required in treating pelvic incontinence and prolapse disorders.

Although these traditional mesh implants have had a tremendous benefit for those suffering from incontinence and prolapse, there is still room for improvement. As a result, there is a desire to obtain a uniquely applicable, minimally invasive and highly effective implantable mesh support that can be used to treat incontinence, organ prolapse and other pelvic disorders and conditions.

SUMMARY OF THE INVENTION

The present invention describes implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle or ligament weakness. Other uses include providing a support or platform for plastic surgery, hernia repair, and ortho repairs and support, to name a few. Embodiments of the implants can include a tissue support portion and one or more extending arms or anchoring portions.

In various embodiments, the implants can be formed of patterned cells by way of a molding, die casting, laser etching, laser cutting, extruding, and the like. Such a pattern cut or formed implant can be constructed of a polymer material to provide a lattice support structure of repeated cells. Unlike woven or knitted conventional implants, the implants of the present invention are a homogeneous unitary construct.

Portions of the implant can be formed into sinusoid or other waveform strut members to control and promote elongation, expansion or contraction along single or multiple axes. As such, controlled and designated stress, tension and compression distribution is promoted across specific or localized areas of the construct. Further, the implant can be formed such that regions or portions can include anchoring features to facilitate engagement and attachment of the implant to target tissue sites. In addition to anchoring to internal tissue, it is also possible to have one or more portions of the implant extend out of an incision or orifice in a patient.

In addition, each patterned cell of the implant can include uniquely shaped or cut strut members configured to define cell voids, to optimize or increase tissue in-growth, to promote load bearing along select portions of the implant, to compensate for stiffness, elongation, compression, and tensile strength. The material and cell construct of the implant can be configured to promote flexibility while still providing optimal implant strength and tissue support. Further, the stable geometrical and dimensional attributes of the implant provide a flexible device that can be easily positioned and deployed while also avoiding undesirable implant warping or bunching.

One or more anchoring portions can include an anchor rod or member extending out from the implant, with a tissue anchor provided at the distal end of the rod. The anchor rod can be an undulating anchor rod having one or more curved or arcuate bends to facilitate adjustment and tensioning.

Various anchor devices are provided with various embodiments, including anchoring mechanisms for connecting to the film or generally unitary body of the implant.

In addition to molding and laser cutting the struts and other features of the implant, punching, 3-D printing and other methods and techniques can be employed in making the implant. Further, the struts or other portions of the implant can be coated to provide additional control over expansion, compression, and to protect from or promote tissue in-growth.

The implants, or portions thereof, can be adapted to provide desirable adjustability, stress distribution, anchoring, stabilization, variable elongation, and the like.

BRIEF DESCRIPTION OF THE DRAWINGS

FIGS. 5-8 are top views of different sized patterned implants having undulating anchor rods, in accordance with embodiments of the present invention.

FIGS. 17-21 are exemplary paddle measurement devices, in accordance with embodiments of the present invention.

FIGS. 40-41 are views of an anchor, suture and mesh arm attachment device, in accordance with embodiments of the present invention.

FIG. 42 is a view of a buckle-like mesh anchor arm attachment device, in accordance with embodiments of the present invention.

FIG. 43-45 are views of implants having anchor arm attachment apertures and devices, in accordance with embodiments of the present invention.

DETAILED DESCRIPTION OF PREFERRED EMBODIMENTS

Figure 1:
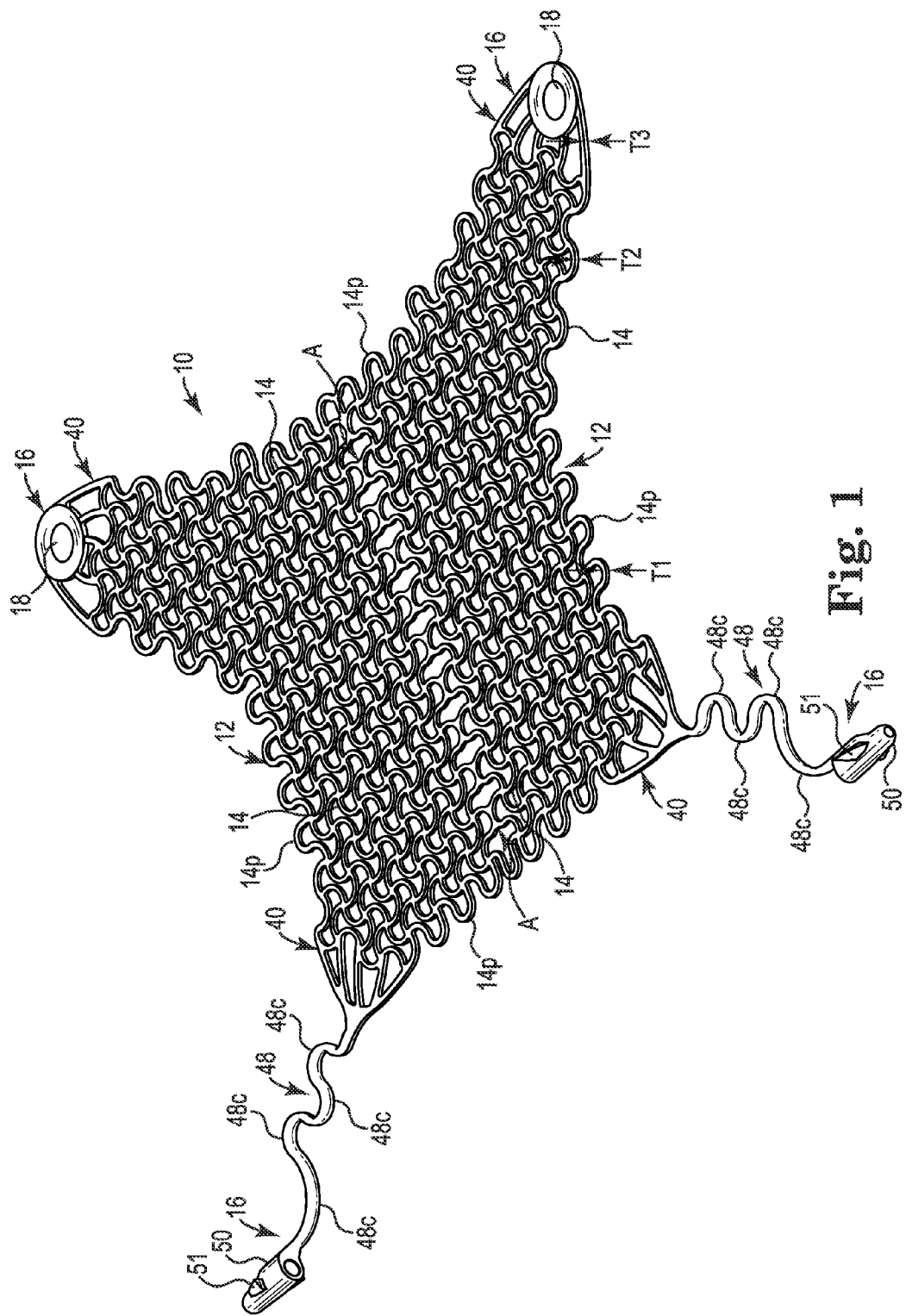
FIGS. 1-2 are views of a unitary patterned implant with undulating anchor rods, in accordance with embodiments of the present invention.

Referring generally to FIGS. 1-50, various embodiments of a patterned implant 10 and methods are shown. In general, the implants 10 can include a support portion 12 and anchoring portions 16. Various portions of the implant 10 can be constructed of polymer materials, e.g., into a molded generally planar structure or from a thin generally planar film or sheet material. Examples of acceptable polymer materials available in constructing or forming the implant systems 10 and its components can include polypropylene, polyethylene, fluoropolymers or like biocompatible materials.

The implants 10, and portions thereof, could take on a myriad of different sizes, shapes and configurations depending on the particular treatment application, or deployment and support needs. For instance, certain configurations can be for uterine sparing prolapse repair and others for the post hysterectomy patient.

The various implants 10, structures, features and methods detailed herein are envisioned for use with many known implant and repair devices (e.g., for male and female), features, tools and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2011/0124956, 2011/0144417, 2010/0261955, 2002/151762 and 2002/147382. Accordingly, the above-identified disclosures are fully incorporated herein by reference in their entirety.

Referring generally to FIGS. 1-13, various embodiments of the implant 10 are shown. Portions of the implant 10, such as the support portion 12, can be formed or patterned by way of a polymer molding process to create a unitary homogeneous non-woven, or non-knitted, device or construct. Other embodiments can be formed from an already unitary homogeneous sheet or film via laser cutting, die cutting, stamping and like procedures.

As a result of the manufacturing process, molding or cutting, repeating cells form a lattice structure for at least the support portion 12 of the implant 10. Portions of the implant can be formed into sinusoid, or other waveform or undulating struts 14 to control elongation or compression along single or multiple axes, to define a desirable pattern density with overall reduced surface area, and to control the distribution and shaping from applied loads. The ability to mold, form or cut the struts 14 in a nearly endless array of sinusoidal or like configurations provides an implant 10 that can better tailor or mimic the anisotropic behaviors of physiological tissue.

One or more portions of the implant 10 can be constructed of a polymer coated, or impregnated or molded with a coloring. As such, the entire implant 10, or simply a portion of the implant such as the support portion 12, can be colored to stand out relative to the surrounding tissue. Coloring (e.g., blue) of the implant or implant portions can improve visualization and positioning of the implant 10 by the physician during implantation by providing desirable surface contrast. Further, various embodiments of the implant 10 can be constructed of opaque, or translucent, polymer materials.

In certain embodiments, such as those depicted in FIGS. 1-4, the patterned struts 14 define a general pinwheel design including first angular strut lines 20 and second angular strut lines 22 crossing or intersecting at repeating fixed junctions 24 to define cellular voids 26. The thickness, size and separation of the struts 14 can be modified to create an implant 10 with different surface area and cellular density attributes.

By arranging the density of the cell patterns with the embodiments of the implants 10 of the present invention, it is possible to tailor the elongation, load or strength properties of the implant 10 according to specific needs and support requirements. Moreover, more than one material can be used to construct the implant 10 to further control desired load and stress properties, e.g., combining different polymers such as polypropylene, PEEK, PET, PTFE, PGA, PLA, etc. Polymers could also be combined with metallic elements to alter strength and elongation profiles of the implant 10. The stronger materials would take up stresses from higher load regions faster, thereby allowing for a method to selectively control performance characteristics of the implant 10. Moreover, a polymer or metal frame could be provided along the periphery or other select areas of the implant 10 to provide additional strength or rigidity properties.

Figure 2:
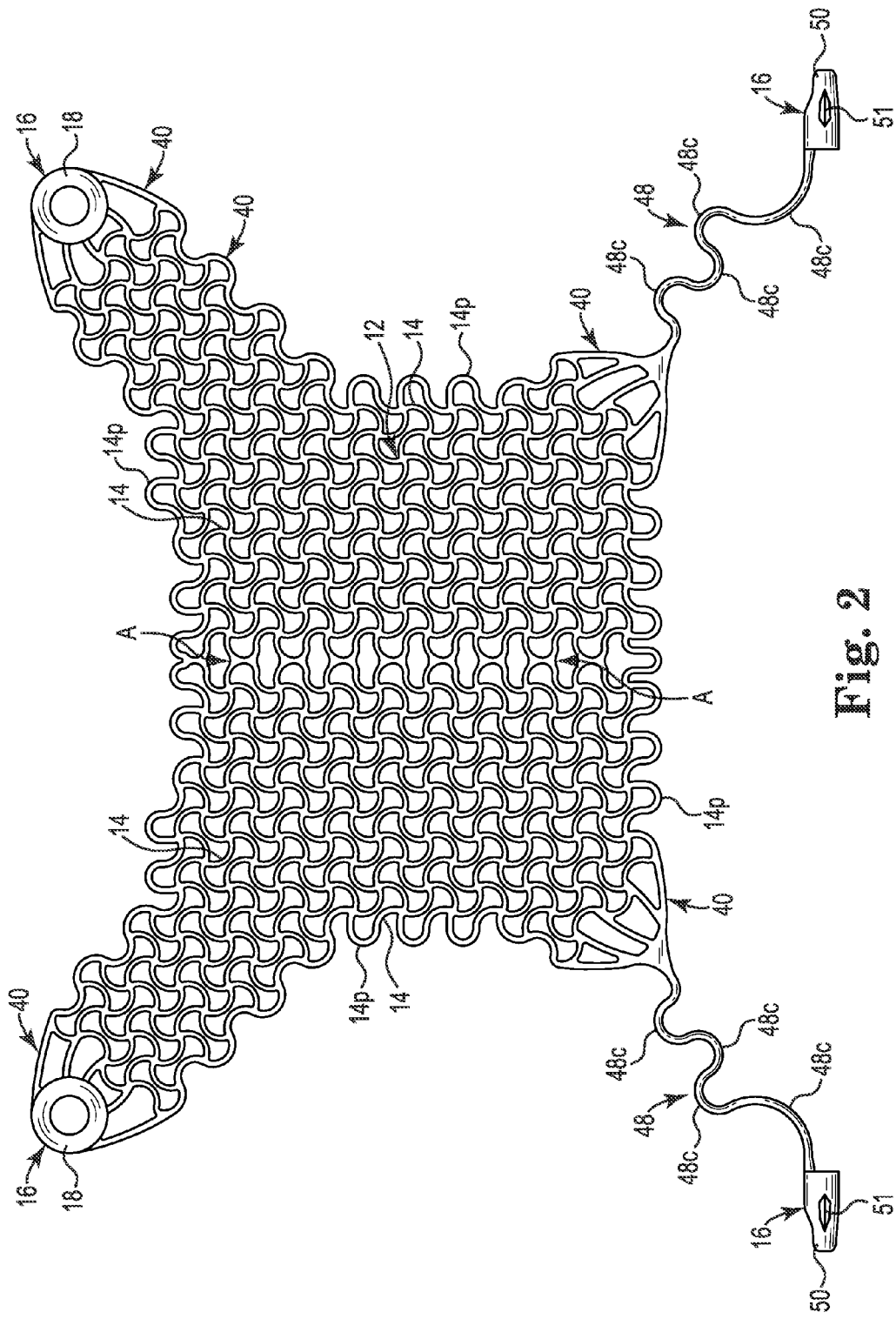
Figure 3:
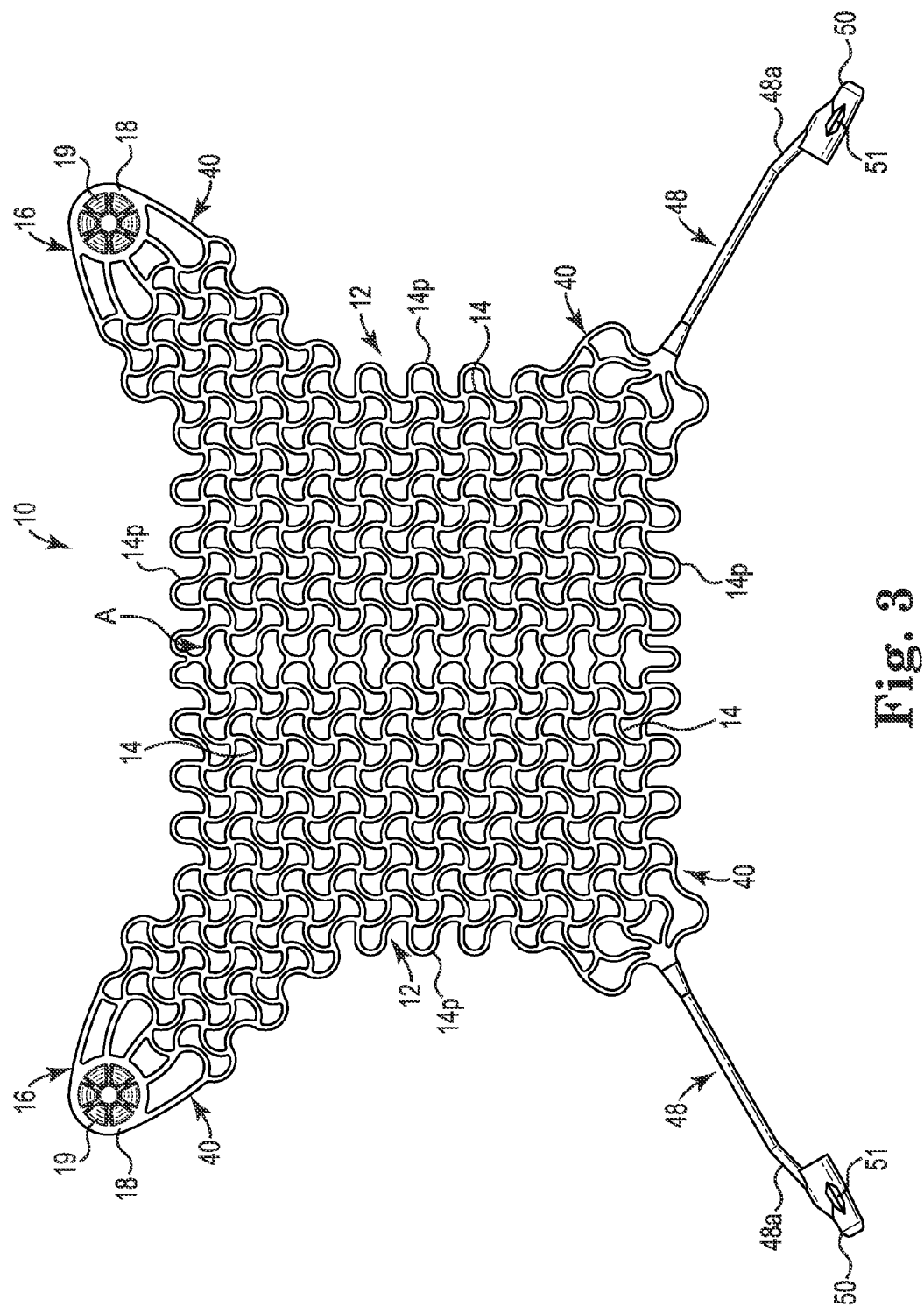
FIG. 3 is a top view of a unitary patterned implant having anchor rods with an angular bend, in accordance with embodiments of the present invention.
Figure 4:
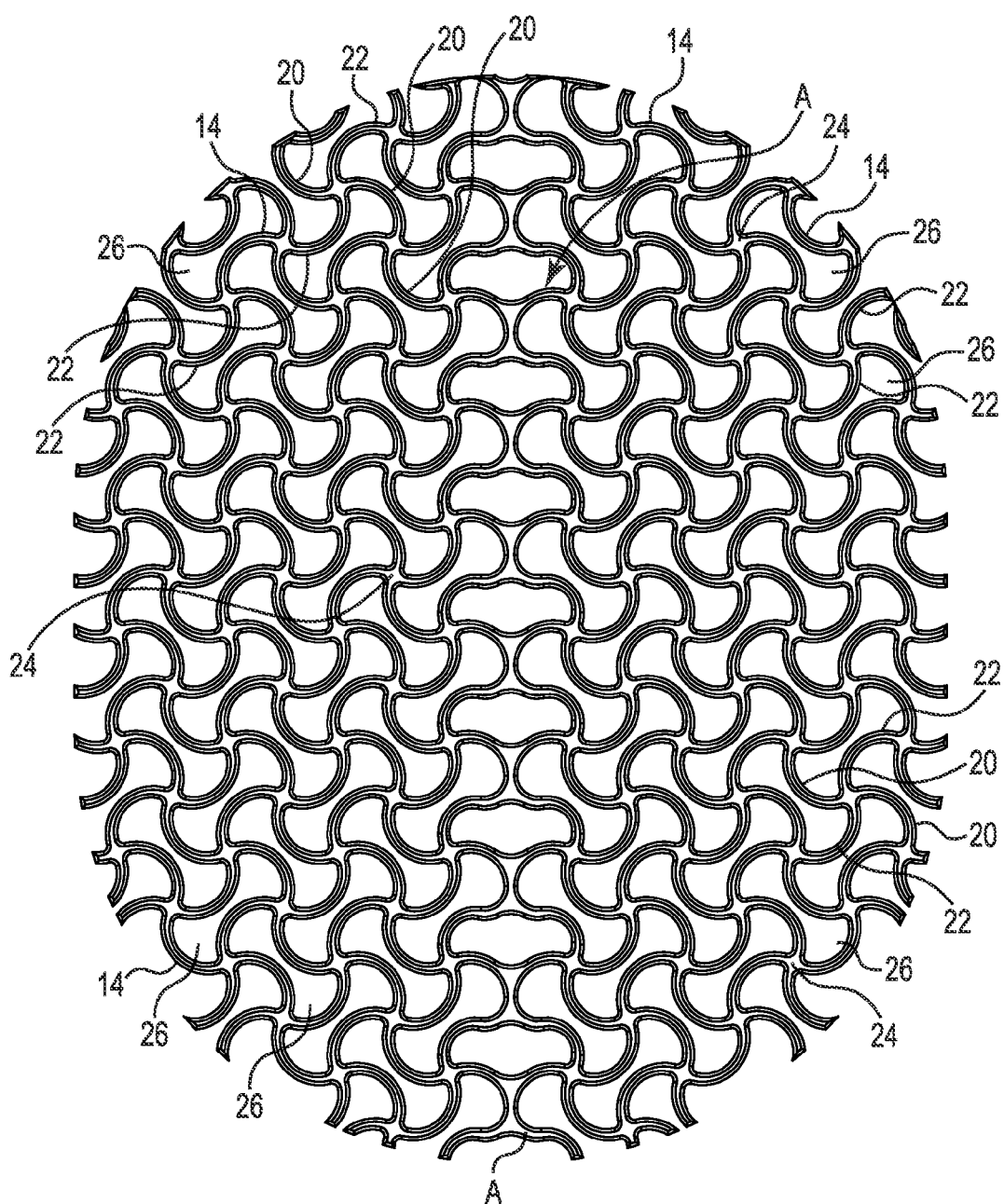
FIG. 4 is a partial close-up schematic view of struts, cells and a central support axis for a unitary patterned implant, in accordance with embodiments of the present invention.

As demonstrated in FIGS. 2-4, embodiments of the implant 10 can include a symmetry axis or structure A. The axis A can take on a unique shape and configuration as shown in the figures to provide desired compression and expansion characteristics generally central to the width or length of the implant 10. Alternatively, the axis A can take on shapes and dimensions similar to that of the surrounding sinusoidal cell configurations. In addition to providing physical compression and support characteristics, the axis A can serve as an important marker or line of reference during implantation. As such, the axis can be colored or otherwise marked to visually stand out relative to the implant 10 as a whole. In various embodiments, the axis A can be colored or marked along a length shorter than its entire length. Variations on the visual marking of the axis A are envisioned for embodiments of the present invention.

The dimensional design of the implant struts 14 can be configured to promote targeted strength and flexibility. For instance, the material width at the fixed junctions 24 can be measurably greater than the material width of the struts 14 intermediate the junctions 24 to allow for increased strength at the junctions. Strengthened and widened junctions 24 can handle and absorb greater stress or torque resulting from implant positioning, twisting and general manipulation. Conversely, thinner strut portions 14 intermediate the junctions 24 promote can increase flexibility and controllability of the implant 10 during positioning and device manipulation. This flexibility will also provide an implant 10 adapted to properly conform to unique patient anatomy and lay flat against such anatomy to provide optimal support distribution, tissue in-growth and like characteristics. In one embodiment, the junctions 24 can range in material size or width from 0.017 inches to 0.020 inches. The intermediate strut portions 14 can range in material size or width from 0.014 inches to 0.017 inches. Other dimensional ranges and proportions are envisioned for embodiments of the struts and strut portions depending on the particular application, strength, flexibility, stress distribution or other performance needs of the implant. Of course, the structures of the implant 10 can be provided in other sizes as well.

The struts 14 and cells can extend to provide or define a strut perimeter 14p that can include the looped or curved shape of the cells to provide atraumatic cell geometry. For example, such a configuration provides an implant 10 with perimeter structures that minimize or eliminate poking or snagging on tissue within the patient during implantation and after.

Additional benefits are presented with the homogenous non-woven design and targeted strength regions (e.g., fixed junctions 24) of the implant 10. Namely, a flexible but strong implant 10 is provided, while still maintaining a low surface area, lower inflammatory response, less scarring and increased density.

The patterned implant 10 also provides benefits over traditional knitted or woven mesh in the area of compression and the reaction to longitudinal extension strain. Traditional knitted or woven mesh implants can tend to compress and narrow during longitudinal stretching, thereby displaying a positive Poisson affect or ratio. Conversely, the sinusoidal cell and strut configurations of certain embodiments of the patterned implants 10 of the present invention can display a Negative Poisson affect or ratio. In particular, as the implant 10 is loaded or stretched (e.g., at ends, anchors, corners or upon the planar surfaces), the strut and cell structures can resist compression and measurably expand to provide a stable and generally planar surface area for tissue or organ support. The combination of the struts and fixed junctions facilitate this Negative Poisson affect.

The cross section of the non-woven strut members 14 are generally circular, oval or otherwise formed to have rounded portions with exemplary embodiments of the present invention. This is a significant advantage over the bunched woven or knitted filament mesh stands of conventional implants. The rounded portions of the struts 14 of the present invention provide an improved implantation feel and a consistent surface adapted to lay flat and retain its shape against target tissue, and to reduce or eliminate snagging or resistance during deployment and positioning. In addition, it provides a desirable tactile feel and surface for the physician to grasp and manipulate during implantation, and as the implant 10 passes along tissue.

Embodiments of the implant 10 can include one or more transition portions or zones 40, as shown in FIGS. 1-3. In general, the zones 40 provide a material transition between the cellular construct of the support portion 12 and anchoring or like features 16 of the implant 10, e.g., anchors, eyelets, etc. The transition zones 40 can take on various sizes, shapes and designs to provide increased strength and stress absorption/distribution for portions of the implant 10 being pulled, pushed and twisted during deployment and positioning of the implant 10. Embodiments of the zones 40 can include arcuate lattice or cell structures fanning out from or into the support portion 12 and the anchoring portions 16. The zones 40 can be tapered into or away from the support portion 12 or anchoring portion 16 to facilitate stress and tension distribution such that the struts 14 and cell structures of the support portion 12 are protected from tearing, ripping or other material breaches.

The structure and design of anchoring features of portions 16 of the implant 10 can vary greatly depending on the particular implantation and support needs of the particular device. In certain embodiments, the anchor portions 16 can include first and second anterior and opposing anchors extending out angulary from an anterior end region of the implant 10. A tissue anchor 50 is provided at a distal end of the anchor rod 48 such that the rod 48 extends intermediate the anchor 50 and the transition zone 40. The tissue anchor 50 can include one or more tines 51 adapted to engage and/or penetrate soft tissue, e.g., the obturator internus muscles. The anchor rod 48 can be generally cylindrical in certain embodiments, or generally flat or rectangular in other embodiments. The anchor rod 48 is adapted to absorb and comply with twisting or other like motions imposed on the anchor portion 16 during deployment and positioning of the implant 10.

FIGS. 1-2 and 5-8, for instance, depict various embodiments of the implant 10 having undulating anchor rods 48. Undulating or curved sections 48c facilitate stretching and accommodation for anatomical variation in prolapse patients, or other treatment uses. Again, one or more arcuate, curved or transitional bend portions 48c can be included along the length of the rods 48 between the transition portion 40 and the anchor 50. Embodiments can include a different number of curved sections 48c (e.g., one, three, four, five, etc.) depending on the anatomical structure of the patient, the size of the bends, the length of the rod, or other procedural and structural considerations. As depicted, the curved sections 48c can be defined by bends of varying radiuses and lengths. For instance, the curved section 48c proximal the anchor 50 can have a generally larger length and radius (e.g., compared to the curved sections 48c nearest the transition zone 40) such that the anchors 50 are provided in an anchoring position and orientation ideal for the particular tissue path and target tissue site. The rods 48, and corresponding sections 48c, can be constructed of a polymer or like material as disclosed herein, such that it can be pulled on to expand or extend the length of the rod 48 at the sections 48c to allow for adjustability and the anatomical variations in patients.

Further, sections of the anchor portion 16, including the anchor rod 48, can be generally rigid, or flexible, depending on the particular strength and anchor displacement needs. In addition, the anchors 50 can be rotatably or pivotably affixed to the rods 48, any other portion of the anchor portions 16, or the transition zones 40. Any of the anchors depicted or described herein can be integrally formed with a portion of the implant 10, or separately attachable or detachable therefrom.

FIG. 3 shows an embodiment of the implant 10 including a generally linear rod 48 having an angular bend 48a section (e.g., off-axis). The end of the angular bend 48a can include an anchor device 50. As such, the anchor device 50 is adapted to better accommodate and engage with a tip of a needle, as described herein, to reduce or eliminate interference of the needle and facilitate corresponding navigation to engage the anchor 50 in the target tissue to locate the implant 10 for support and treatment.

Further, embodiments of the implant 10 can be constructed in various dimensional and proportional configurations, as shown in FIGS. 5-8. Namely, the overall shape and size (e.g., width and length) of the implant 10 can vary depending on the particular procedural needs for the patient. The various optional implants 10 can be included in a surgical kit for the physician to select from before or during a particular treatment procedure. The inclusion of various sized and shaped implants 10 can be used as an alternative to providing a single implant 10 with tails or other portions that can be removed or added. In addition, multiple configuration options enables deployment of the implant 10 into patients having different anatomical features, dimensions and geometry.

Figure 5:
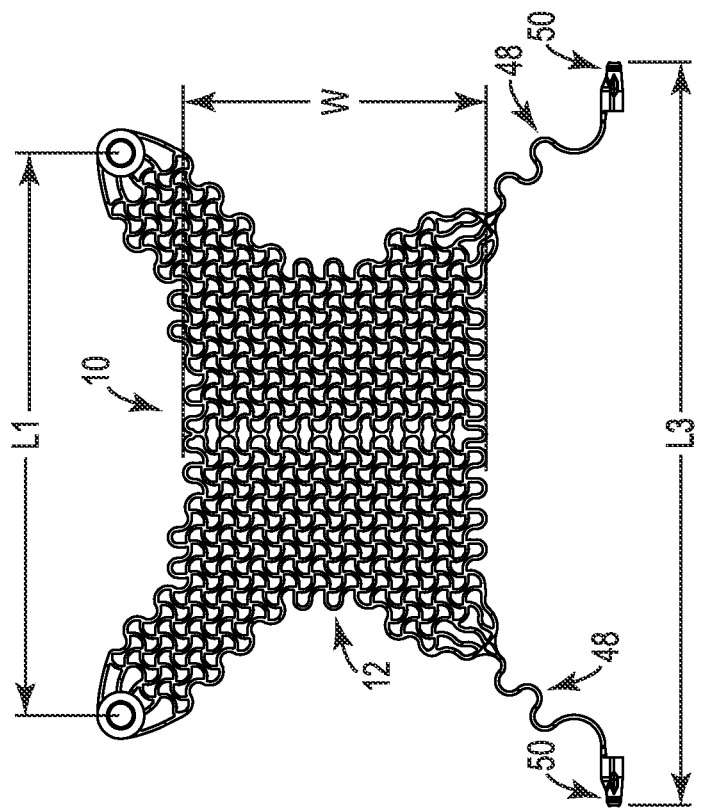
Figure 6:
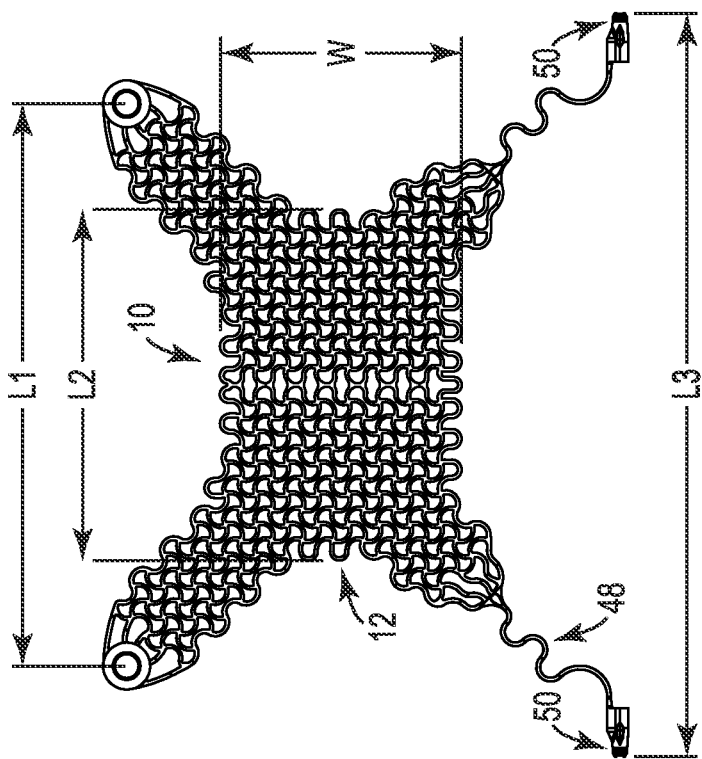
Figure 9:
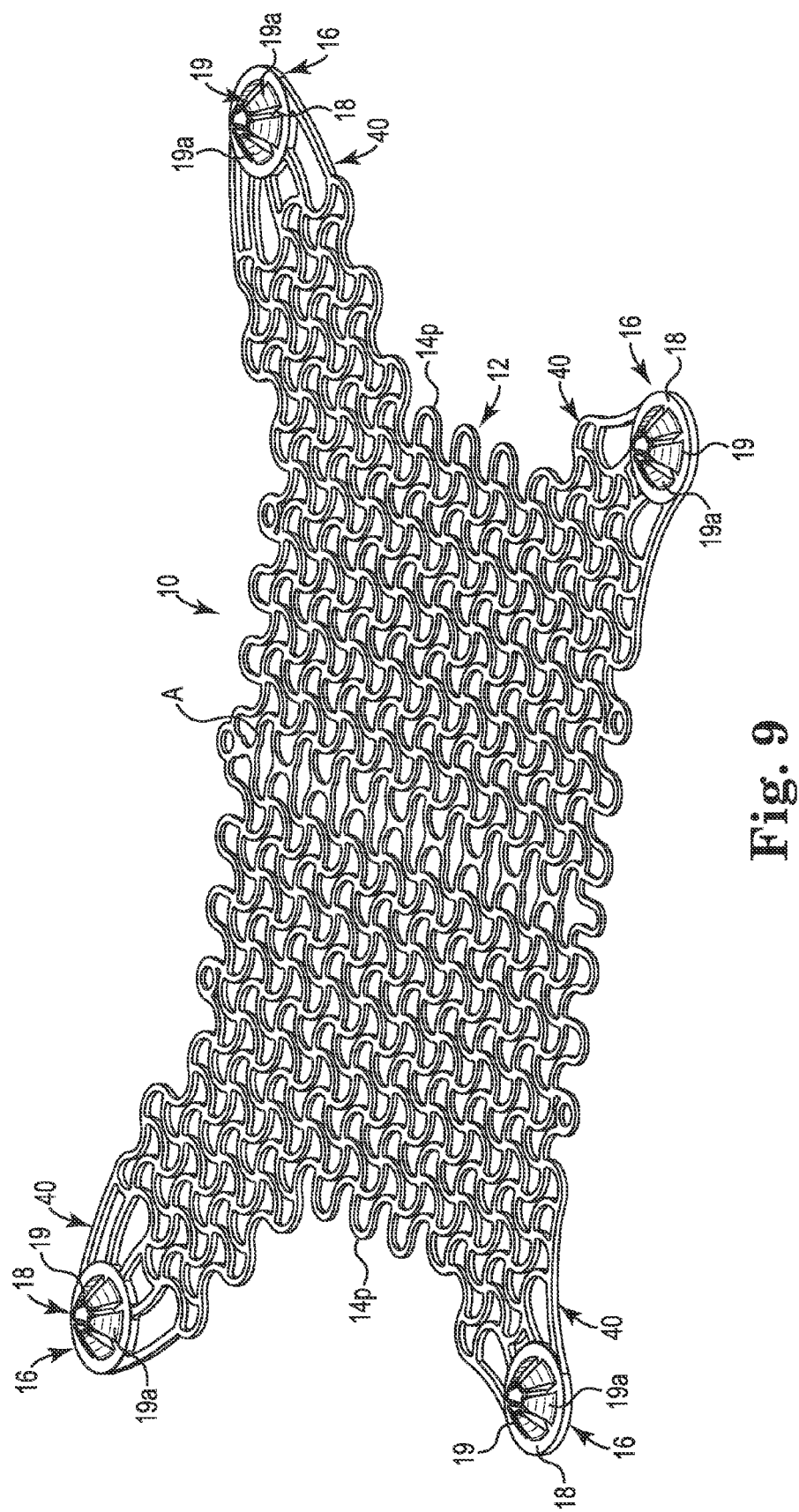
FIGS. 9-10 is a perspective view of a patterned implant having eyelets and grommets, in accordance with embodiments of the present invention.
Figure 10:
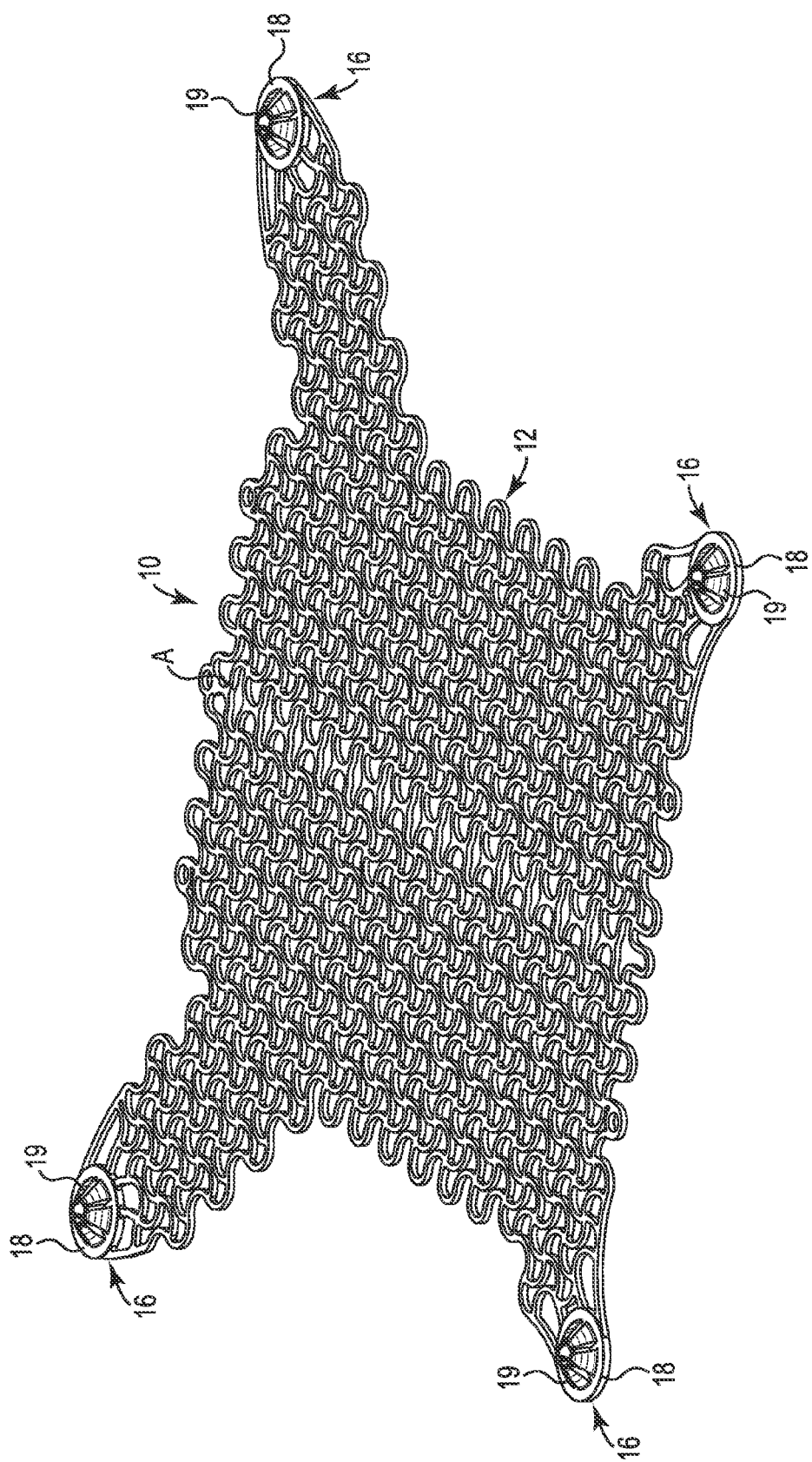

FIGS. 5-6 demonstrate two smaller embodiments of the present implant 10 defined by various length dimensions L1, L2 and L3, as well as width dimensions W. While a myriad of acceptable dimensional configurations are envisioned for use with the present invention, depending on the particular patient and surgical requirements, these figures depict exemplary configurations.

For instance, as shown in FIG. 5, the distance between the two eyelet or other top anchoring portions, L1, can be approximately 74 mm; the distance between certain transition zones, L2, can be approximately 47 mm; the overall distance between the bottom anchors, L3, can be approximately 98 mm; and the width of the support portion, W, can be approximately 32 mm. For the embodiment of FIG. 6, the distance between the two eyelet or other top anchoring portions, L1, can be approximately 74 mm; the overall distance between the bottom anchors, L3, can be approximately 98 mm; and the width of the support portion, W, can be approximately 40 mm.

Two generally larger implants 10 are depicted in FIGS. 7-8. As demonstrated with the embodiment of FIG. 7, the distance between the two eyelet or other top anchoring portions, L1, can be approximately 82 mm; the overall distance between the bottom anchors, L3, can be approximately 98 mm; and the width of the support portion, W, can be approximately 46 mm. As shown in FIG. 8, the distance between the two eyelet or other top anchoring portions, L1, can be approximately 74 mm; the length of the support portion (or the general distance between transition portions), L2, can be approximately 46 mm; the overall distance between the bottom anchors, L3, can be approximately 98 mm; and the width of the support portion, W, can be approximately 54 mm. Again, various other configurations and dimensional embodiments can be included without deviating from the spirit and scope of the present invention.

A grommet 19 (or locking eyelet) or blocking eyelet structure can be provided integral with an eyelet 18. The blocking eyelet 19 can a member or feature molded into the grommet 19 to allow for release of grommet teeth during implantation to allow for removal or back tracking of the anchor arm or like device from the grommet 19. However, other embodiments can include a separately engageable grommet 19 component, as previously depicted and disclosed (e.g., FIG. 1). The various dimensional values shown in these figures are for illustrative purposes only.

Referring generally to FIGS. 3, and 9-12, the support portion 12, or the anchor portions 16, can include one or more eyelets 18, with transitioning zones 40 extending or spanning intermediate the eyelets 18 and the strut 14 cell structures. An aperture extends through each of the eyelets 18. The eyelets 18 can simply include corresponding apertures for engagement with anchoring members or devices, or the eyelets 18 can be integrally formed with a grommet 19 having a plurality of extending or angular teeth 19a. In other embodiments, the grommet 19 can be separately attached or seated.

The teeth 19a are adapted to engage and retain various anchoring structures, such as anchor mesh, separate anchor members, extensions, apertures or protruding members. The eyelets 18, and any corresponding material or structures associated with the eyelets 18, can be provided along any side, end or body portion of the implant 10, depending on the particular anatomical and treatment application. Moreover, a variety of sizes, quantity and shapes are envisioned for the eyelet 18 configurations for embodiments of the implant 10. For those embodiments having an integrated grommet portion, the configuration can result in a reduced mass or low profile locking eyelet, compared to those where a separate and distinct grommet is provided.

FIGS. 9-12 show exemplary embodiments of the implant 10 having exemplary eyelet 18 and support 12 configurations, shapes and designs, which not require integrated anchor rods 48. Again, numerous shape and size configurations can be employed depending on the particular deployment and treatment uses for the implants 10. As explained herein, the grommet portions 19 can be integrated with the eyelets 18 (e.g., as a reduced mass or low profile locking eyelet) or separately engaged when slid along a separate anchor arm.

Various thickness and size differences between the various areas (e.g., 12, 18, 40, etc.) are shown as well. These unique structural constructs can be implemented so that various portions of the implant 10 are thicker and stronger (e.g., 18, 40) to handle the twisting and torque of deployment and adjustment, while other portions or struts (e.g., 12, 14) can be thinner to promote flexibility and manipulation.

Figure 12:
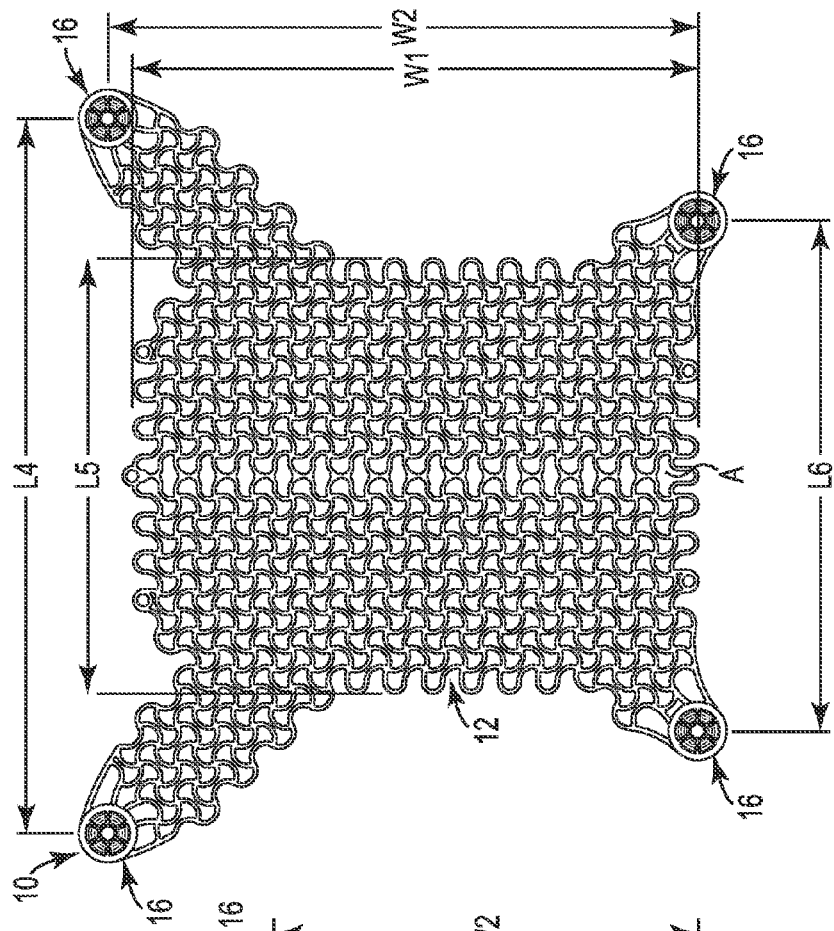
FIGS. 11-12 are top views of different sized patterned implants having eyelets and grommets, in accordance with embodiments of the present invention.
Figure 11:
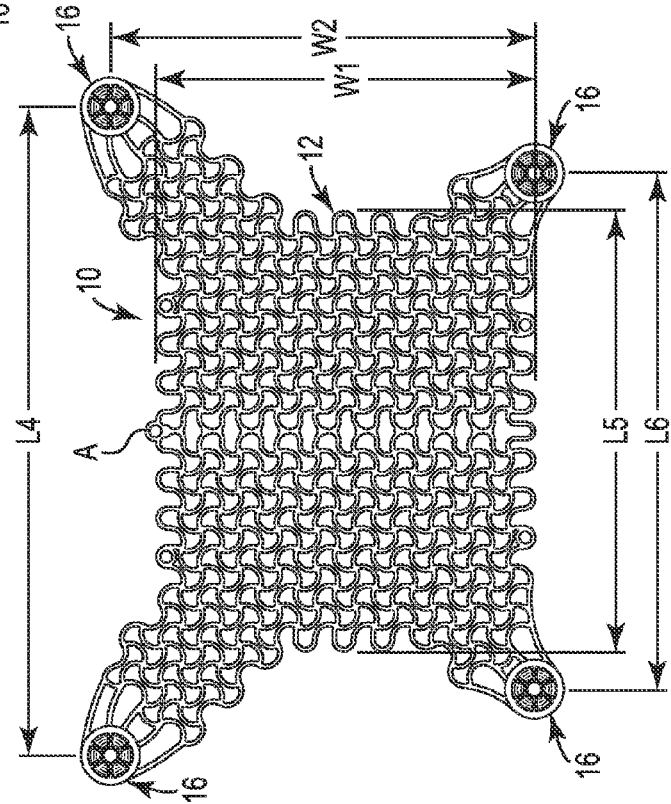

As demonstrated with the embodiment of FIG. 11, the distance between the two top eyelet or anchoring portions, L4, can be approximately 68 mm; the length of the support portion, L5, can be approximately 46 mm, the overall distance between the bottom eyelet or anchoring portions, L6, can be approximately 54 mm; the width of the support portion, W1, can be approximately 40 mm; and the width or distance form the top eyelet portions to the bottom eyelet portions, W2, can be approximately 45 mm. As shown in FIG. 12, the distance between the two top eyelet or anchoring portions, L4, can be approximately 76 mm; the length of the support portion, L5, can be approximately 46 mm, the overall distance between the bottom eyelet or anchoring portions, L6, can be approximately 54 mm; the width of the support portion, W1, can be approximately 60 mm; and the width or distance form the top eyelet portions to the bottom eyelet portions, W2, can be approximately 63 mm. Again, various other configurations and dimensional embodiments can be included without deviating from the spirit and scope of the present invention.

Figure 13:
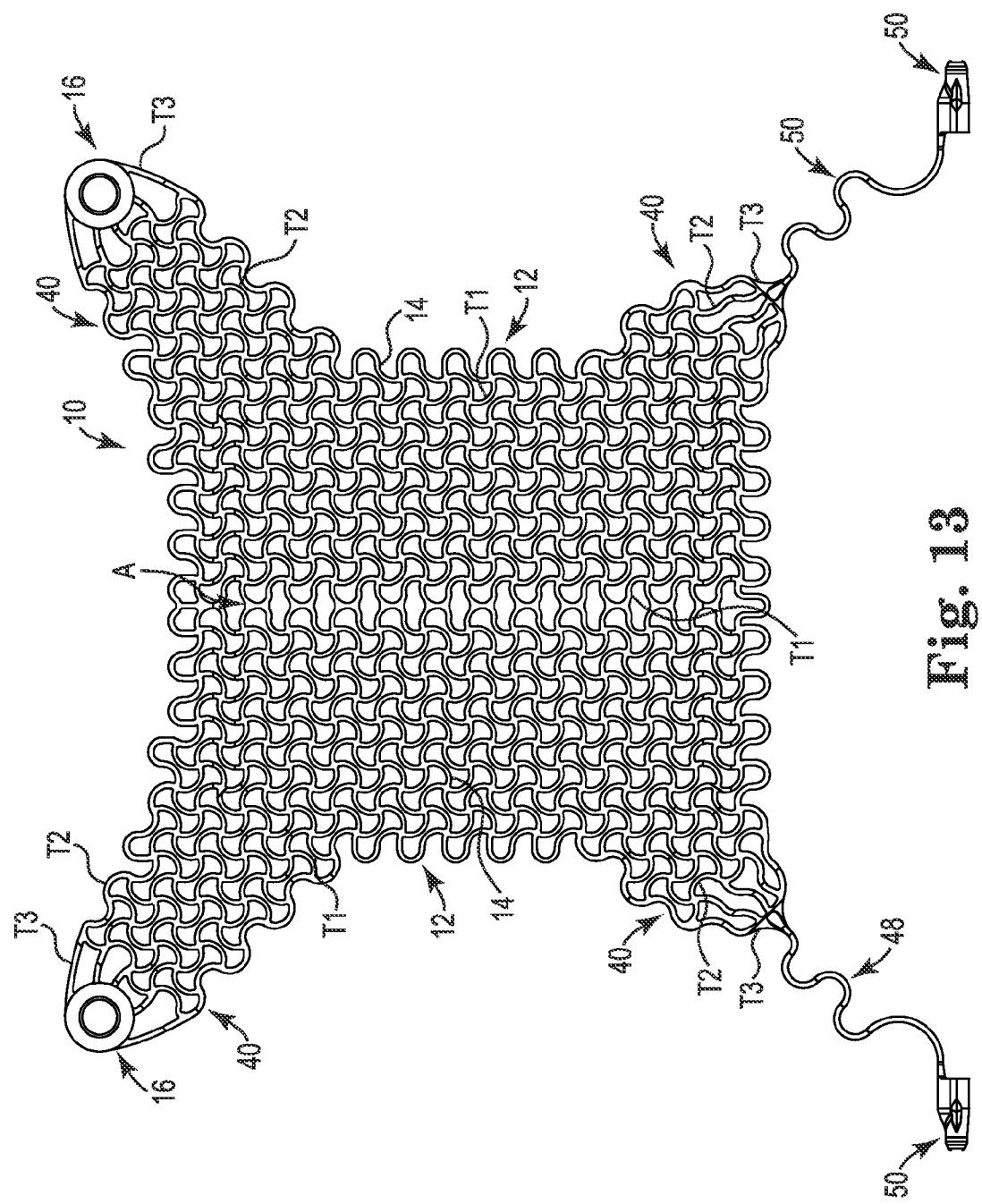
FIG. 13 is a top view of a patterned implant having portions of different thicknesses, in accordance with embodiments of the present invention.

As shown in FIG. 13, embodiments of the implant 10 can include portions constructed of struts 14 or other members having different or varying thicknesses (e.g., depth of strut in cross-section) and/or widths. For instance, at least a section T1 of the support portion 12 can be formed or constructed of struts having a thickness in the range or approximately 0.010 inches to 0.013 inches. Further, struts 14 extending between the support portion 12 and the transition portion 40 can be formed or constructed of struts having a thickness T2. T2, in certain embodiments can be measurably thicker than T1, and in a range of approximately 0.013 inches to 0.015 inches. To provide additional thickness and reduced flexibility, still other portions of the implant 10, including members or struts extending from the eyelet or grommet portions can be defined by a thickness T3, which can be in a range of approximately 0.015 inches to 0.018 inches. In general, the thinner the strut or member is, the more flexible it is. Conversely, the thicker the strut or member is, the more rigid and stable that portion of the implant 10 can be. Thinner portions are preferred for those sections of the implant 10 that need to contour, bend, twist or better conform to the surrounding tissue, or where a portion of the implant 10 requires increased adjustment and twisting capability during deployment and positioning. Thicker sections of the implant 10 are better adapted to withstand higher levels of torque, pressure and tension— e.g., sections of the implant 10 adapted to directly or indirectly anchor to tissue.

One of ordinary skill in the art will understand that a myriad of other shapes, sizes and configurations can be employed based on the teachings provided herein. Further, the implant 10 and support portion 12 can be constructed and sized to serve as an elongate incontinence sling, or as a larger prolapse implant.

Various embodiments of the present invention can include struts 14 that have variable widths or thicknesses, can be tapered, can include apertures, or can include defined shapes and/or patterns, e.g., sinusoids, squares, elliptical, triangular, elbowed, straight, or other simple or complex shapes and patterns. Unique strut 14 designs and cellular patterns can be included within a single implant 10 to provide different zones, having different stress, load distribution or compression characteristics. Other strut 14 designs and patterns can be employed as well to achieve the functionality described and depicted herein.

The implants 10 described herein can be implanted into a patient by use of various different types of surgical tools, including insertion tools, which generally are tools useful to engage and place a tissue anchor or a connector that is secured to an extension portion of an implant. Various types of insertion tools are known, including those in the previously-incorporated references, and these types of tools and modifications thereof can be used according to the present description to install the implant 10.

Figure 14:
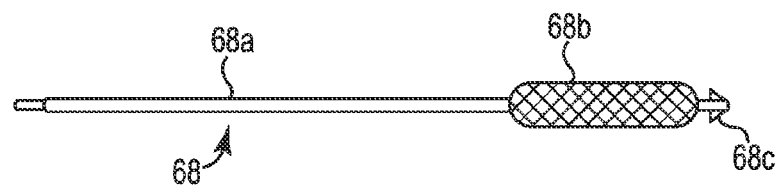
FIG. 14 is an exemplary anchor arm having a rod and a mesh portion, in accordance with embodiments of the present invention.
Figure 15:
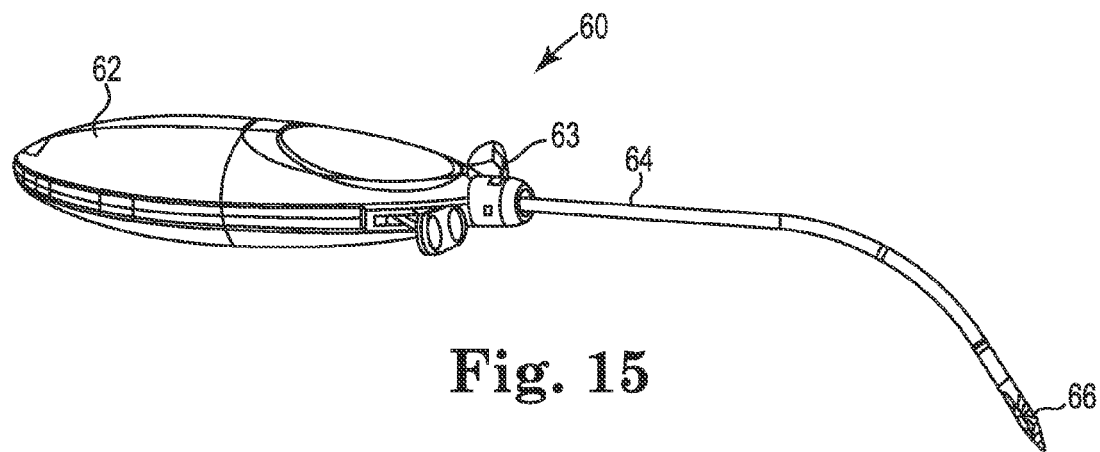
FIGS. 15-16 are exemplary introduction needle tools or devices, in accordance with embodiments of the present invention.
Figure 16:
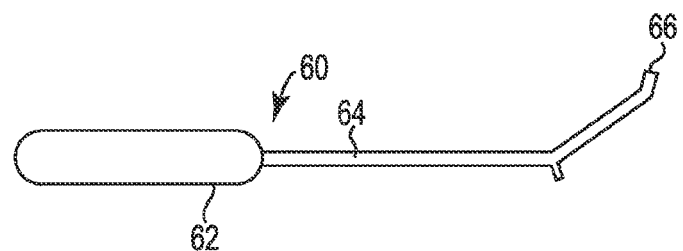
Figure 21:
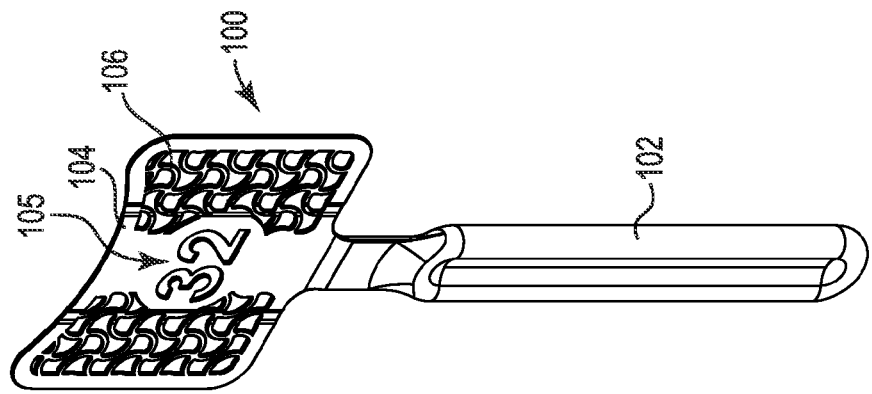
Figure 20:
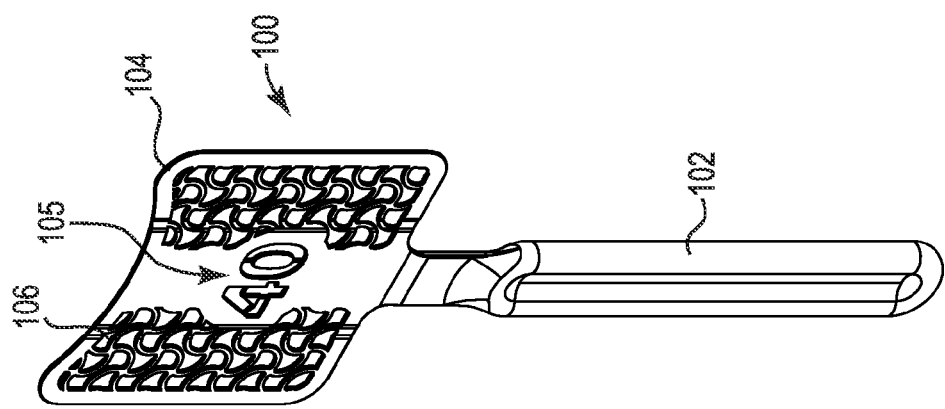
Figure 19:
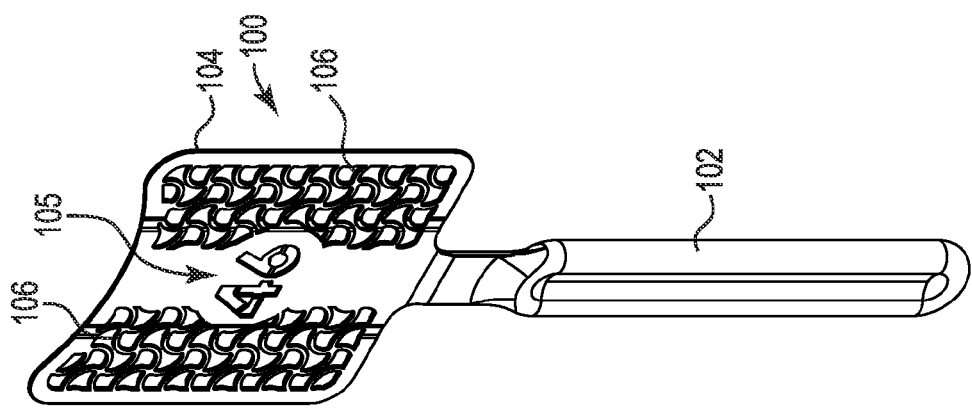

Examples of various insertion techniques and tools are included in FIGS. 14-16, and the incorporated references. Each tool 60 can include a handle 62, needle 64 and engaging distal tip 66. The handle 62 can include an actuation mechanism 63 in operative communication with the distal tip 66 and adapted to selectively control engagement and/or disengagement of the distal tip 66 with portions of the implant 10 (e.g., anchors 50). In various embodiments, the distal tip 66 of a certain tool 60 is adapted to engage with, deploy, position and anchor or insert an anchor fixation arm 68 into the sacrospinous ligament of the patient, with a length or portion of the fixation arm 68 fed through and secured to the eyelet 18 and grommet 19 feature of the implant 10. The anchor fixation arm 68 can include a rod or extension 68a, a mesh portion 68b, and a distal anchor 68c. Certain embodiments of the anchor fixation arm 68 can include an external sheath adapted to shroud portions of the arm 68 during deployment (e.g., the mesh 68b and anchor 68c).

In one embodiment of the surgical procedure for implanting the implant 10 within a female patient to treat vaginal prolapse, an incision is made in the anterior vaginal wall of the patient, and a full thickness dissection is made of the anterior wall. Tissue is generally cleared from the sacrospinous ligaments. The tissue anchors 50 (adapted as anterior fixation anchors) are loaded on to the distal tip 66 of an anterior fixation tool 60. The tissue anchors 50 are then inserted into the obturator internus muscle with a finger-guided needle 60, bilaterally. The implant 10 can be trimmed and sutured to the anatomy as required. Next, the fixation arm 68 is loaded onto a corresponding needle tool 60, advanced through to the sacrospinous ligament and the distal anchor 68c of the arm 68 is inserted through the ligament to provide fixation. Again, an actuation mechanism 63 can be activated to disengage the arm 68 or its respective anchor 68c from the tool 60. Various embodiments of the arm 68 can include an outer sheath or sleeve, which can be removed, such as those disclosed in U.S. Patent Application Publication No. 2011/0112357 and 2009/0240104, each of which is incorporated herein by reference in its entirety. Alternatively, the sheath can remain in place to provide bidirectional adjustment of the arm 68 within the eyelet/grommet aperture configuration of the implant 10. Again, this ligament fixation can occur bilaterally.

Once the arms 68 are fixated within the target ligaments (on each side), the eyelet 18 and grommet 19 on each side of the implant 10 is slid over and along the respective arm 68 (e.g., rod 68a and mesh 68b portions). As such, the grommet teeth 19a will grab onto and secure the mesh 68b of the fixation arm 68 therein. Final tension and adjustment can be provided at the fixation and related portions of the implant 10. Next, excess lengths of the fixation arms 68 extending out from the eyelet 18 can be trimmed and removed. The vaginal incision can then be closed with sutures to complete the procedure.

Various embodiments of a sizing tool 100 are depicted in FIGS. 17-21. The tools 100 can be used by the physician to determine the anatomical geometry and, as a result of the measurement, the correct implant 10 to use for the procedure. The tool 100 can include a paddle-like design having a handle portion 102 and a head portion 104. The handle 102 can include a scale or unit measurement printed, engraved or otherwise provided thereon. The head 104 can include various patterned cell portions 106, and indicia 105 to denote the respective size of the tool. This size marking 105 can match up and assist the physician in determining the appropriate sized implant 10 to use for the procedure. The exemplary embodiments show measurements in millimeters, which can correspond to the measurement of the width W (as described and depicted herein) of the implant 10. As such, the physician can insert the tool 100 into the dissection plane to determine which implant 10 will be best suited for the particular anatomical geometry of the patient and that patient's particular treatment and support needs—e.g., selected from a kit including implants 10 of varying sizes. In certain circumstances, it can be preferred to select an implant 10 slightly smaller than the dissection plane measurement.

Figure 22:
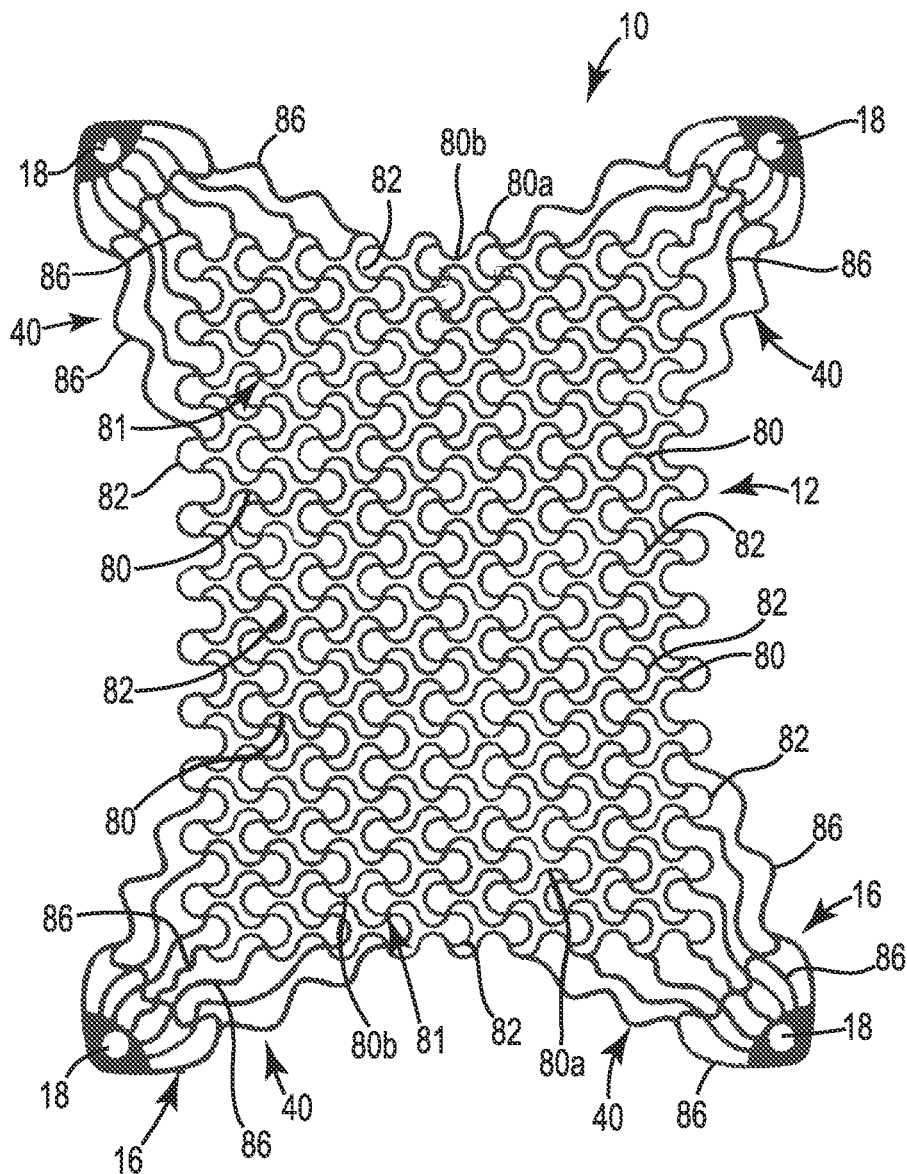
FIGS. 22-23 are views of a patterned implant having sinusoidal and undulating strut cell configurations, in accordance with embodiments of the present invention.
Figure 23:
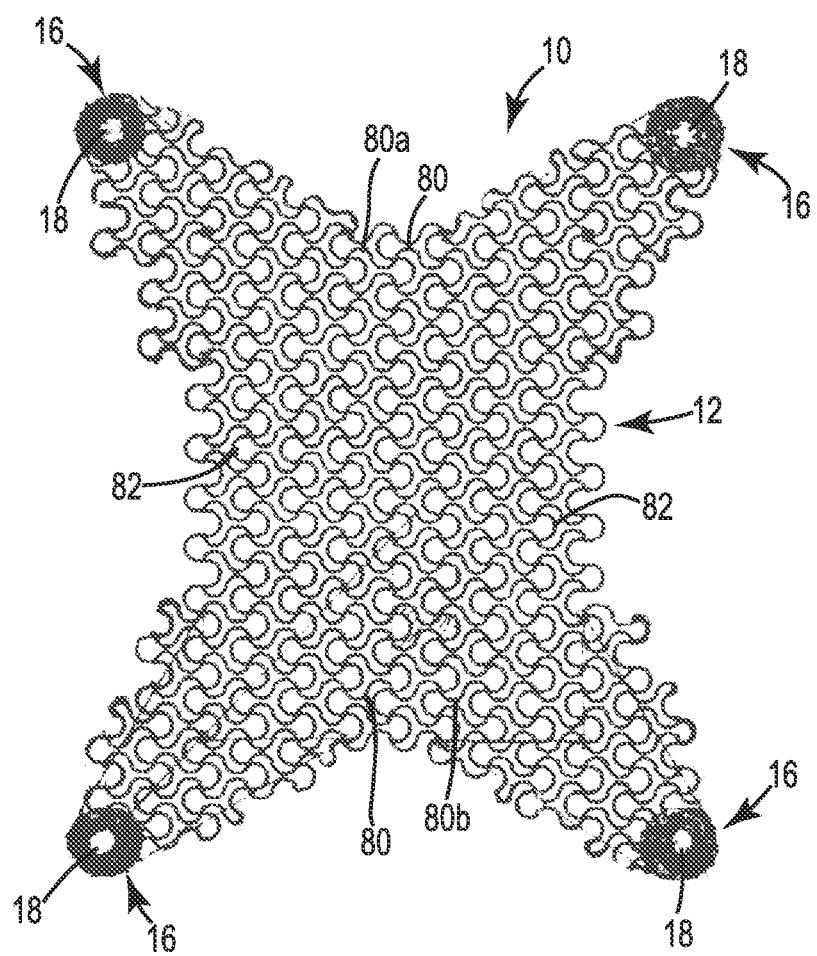

Referring generally to FIGS. 22-23, various serpentine structures to define the strut and cell structures for certain embodiments of the implant 10 is disclosed. An in-phase serpentine pattern with horizontal sinusoidal struts 80 intersecting serpentine struts 82 at centerline point 81, midway between the peaks 80a and troughs 80b of the struts 80 at the general centerline of the serpentines is shown. As the struts 82 are subjected to loading in the longitudinal (vertical) direction, the radii in the peaks and troughs will open and the amplitude will decrease until, ultimately, the stretched serpentine construct becomes nearly straight and extended along the centerline. Torsion will tend to deform the sinusoids somewhat (e.g., opening the angles/radii made with the serpentines). As a result, the overall implant 10 structure, or support portion 12, will tend to expand laterally slightly (widen) as it expands longitudinally (e.g., expands along width W). Further, joining/connecting the sinusoid struts 80 to the serpentine struts 82 in locations off of the centerline can yield mechanical behavior which is desirable in certain situations.

The sinusoid struts 80 can be joined to the serpentine struts 82 at an off-center location. As such, the struts 80 do not quite extend to the centerline of the struts 82. As the struts 82 are expanded and tend toward the centerline, the sinusoidal struts 80 will be placed under tension. Relative to the centerpoints, along a given horizontal row, one end of the struts 80 will be pulled to a position above the centerpoint while the other will be pulled to a position below the center point of the struts 82. As a result of the tensile state of the sinusoid struts 80, the overall structure of the implant 10, or the support portion 12, will tend to decrease laterally (e.g., length L or horizontally) upon expansion. The amount of decrease in the horizontal length can depend upon the location of these attachments. The joining of the struts 80 to the struts 82 at a location short of the serpentine strut centerline can also stabilize the serpentine struts 82. When the struts 82 deform, they can exhibit some out-of-plane bending (that is, the apex points can flare up or buckle out of the plane or into the plane). If the sinusoid struts 80 are attached at locations short of the serpentine centerline, they tend to resist this out-of-plane bending.

The sinusoid struts 80 can also be joined to the serpentines at a location beyond the serpentine strut 82 centerline position. The excess length and over-center positioning of these sinusoid struts 80 can cause them to experience compression as the struts 82 elongate. As a result, the overall structure of the implant 10 will tend to expand or widen horizontally in a manner that is proportional to the location of the attachment of the struts 80 relative to the centerline of the struts 82.

Various implants 10, or support portions 12, can include arrangements of cells including different shapes and constructs, such as polygon shapes. These differently shaped cells (defined again by struts) can, for example, can be included along a portion of the support portion 10 adapted to better support the various organs and anatomical structures around the vagina while permitting the vagina to stretch and elongate, as needed. These different cell constructs can take on a myriad of shapes and sizes, including hexagonal, octagonal, diamond and like-shaped cells arranged in different combinations. These differently shaped cells can be included with (e.g., composite implant 10 or support portion 12), or in lieu of, any of the pinwheel, sinusoidal or serpentine cell constructs provided herein. As such, implants 10 with specialized or targeted mechanical properties can lead to an implant having more precise treatment and deformation characteristics. These various cell and strut constructs can be molded together, laser cut from a thin film or sheet, or defined or joined by various processes and methods.

Various embodiments of the implant 10, as depicted in FIG. 22, can be adapted to expand or elongate slightly in the lateral (horizontal) direction as it deforms longitudinally by including one or more "squid-like" strut arms 86 configured to transmit loads from the anchor portions 16 (such as eyelets) to the support portion 12—e.g., anchors can engage with the obturator internus muscles at the introital end and engage with the sacrospinous ligament at the apical end. The strut arms 86 can have different lengths and thicknesses depending on the locations at which they are joined to the implant 10 or support portion 12.

The various implants 10 and strut configurations described herein can allow for adjustment and tensioning of the implant and anchoring portions during implantation to permit the physician to optimize placement and tension for bladder neck and like support. Further, the anchors can rotate, twist, or pivot during deployment and implantation rather than being held rigidly in one orientation relative to the implant 10. The physician can place the anchors in different locations and accommodate the many different anatomies encountered in the patient population, and adjust the tension of the anchoring for different levels of prolapse around the bladder neck or like anatomical areas.

Various anchoring portions 16, anchor arms, anchors 50 and other means for providing anchoring connections and techniques are also provided with certain implants 10.

Figure 24:
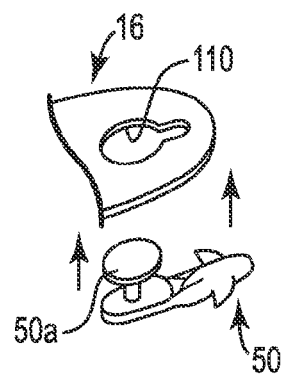
FIGS. 24-25 are views of a key-type anchor attachment device and technique, in accordance with embodiments of the present invention.
Figure 25:
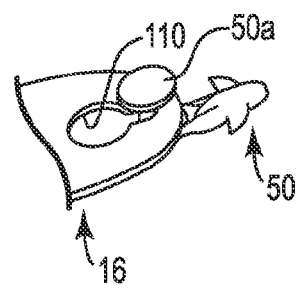

Referring to FIGS. 24-25, the tissue anchors 50 can include an additional molded attachment feature 50a which acts as a key to fit into a keyway, slot or aperture 110 provided with a portion of the implant 10, such as the anchor portions 16. The feature 50a can be generally circular, extend from the anchor 50, and can be pushed through and slid along the slot 110 to lock the anchor 50 in place for implantation. As such, different anchors 50 can be selectively attached to the implant 10 via the slot 110.

Figure 26:
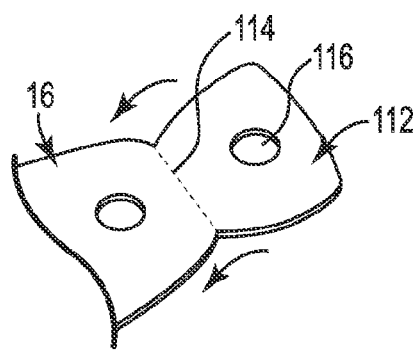
FIGS. 26-27 are views of an extending flap and anchor attachment device, in accordance with embodiments of the present invention.
Figure 27:
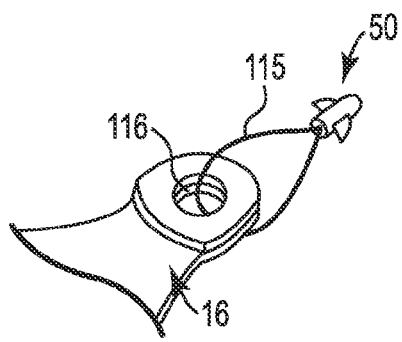

FIGS. 26-27 depict an additional material or feature provided at a portion of the implant 10, such as the anchor portions 16, in the form of a flap 112. This flap 112 can be folded along a hinge or bendable portion 114 (e.g., thinner material construct) over to create a reinforced section of the implant 10 to receive an anchoring device, thereby resisting tearing or material breakdowns when loads are applied to the implant 10 upon deployment. While a suture 115 is shown attaching an anchor 50 to an aperture 116 in the flap 112, other means of connectivity and anchoring can be employed with such an embodiments as well.

Figure 28:
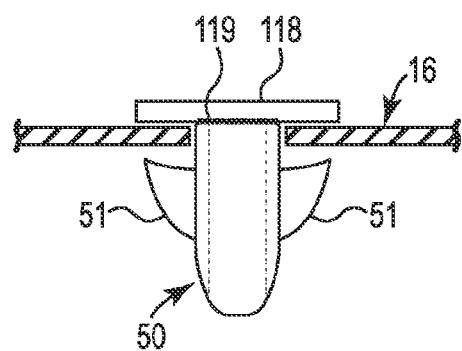
FIG. 28 is a schematic cross-section view of an anchor attachment device, in accordance with embodiments of the present invention.

Referring to FIG. 28, a separate flange element 118 can be pushed through an aperture or portion of the film or unitary implant 10, such as the anchoring portion 16, during manufacturing or formation and then a secondary thermal process can be performed to modify the element 118. This process and structure can serve to bond the anchor 50 to the element 118 at a weldment portion 119 to create a rivet-like configuration for the anchor and implant. The anchor 50 can then rotate as it is not directly bonded to the implant 10, only to the element 118.

Figure 29:
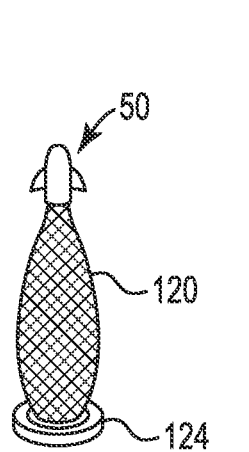
FIGS. 29-30 are views of a mesh arm and anchor attachment device, in accordance with embodiments of the present invention.
Figure 30:
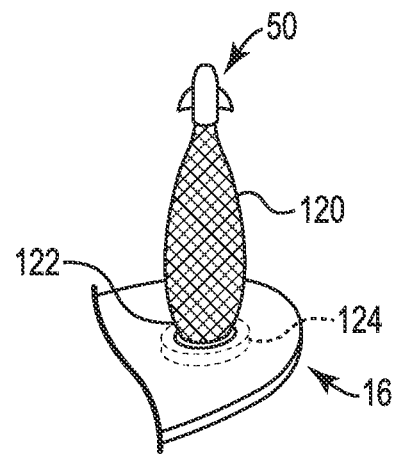

Referring to FIGS. 29-30, the anchor 50 can be attached to mesh material 120, such as a portion of the implant 10, a separate anchor arm, and the like. A section of the mesh 120 is pulled through an aperture 122 in the implant 10, such as at the portion 16, and then a stopper feature 124 is molded or otherwise attached to the mesh 120 at an end opposite the end having the anchor 50. The stopper 124 can be attached to the underside of the implant 10 or portion 16, while still allowing for a wide range of anchor 50 movement, e.g., longitudinal and lateral movement, during deployment and implantation.

Figure 31:
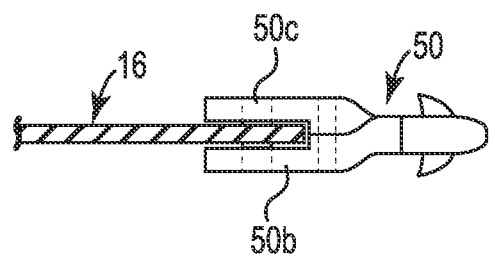
FIGS. 31-32 are schematic cross-sectional views of a two-part anchor and attachment device, in accordance with embodiments of the present invention.
Figure 32:
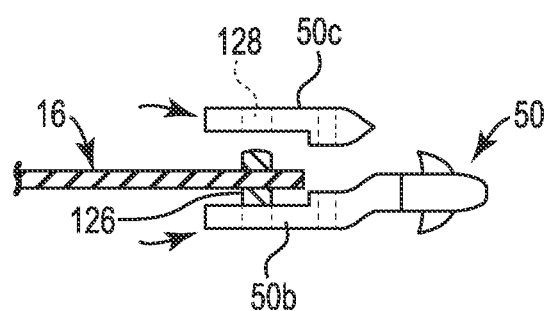

Referring to FIGS. 31-32, embodiments of the anchors 50 can be composed of two separate components 50b, 50c. The components 50b, 50c are placed on either side of a portion of the unitary film implant 10, such as the anchor portion 16, and then pressed or otherwise joined together. The components 50b, 50c can be made to form a snap fit, or can be thermally bonded together with a secondary process. In certain embodiments, a post 126 is provided with at least one of the components, with the other of the components including an aperture 128 to receive and interlock with the post 126. The post 126 likewise extends through an aperture in the implant 10 to provide the disclosed attachment of the anchor 50. As such, a rigid attachment can be provided while still allowing for rotational movement of the anchor 50 relative to the implant 10.

Figure 33:
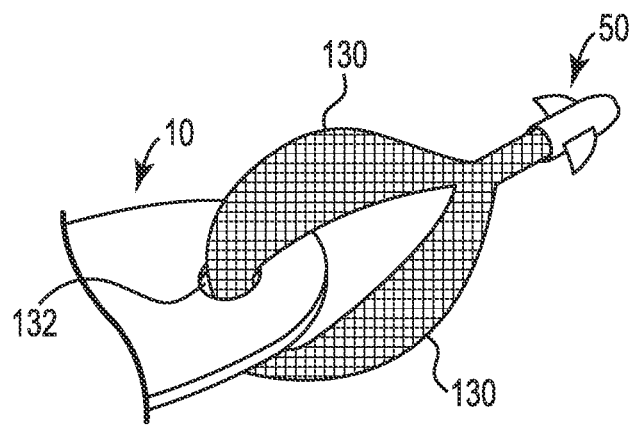
FIG. 33 is a view of a mesh anchor arm and attachment device, in accordance with embodiments of the present invention.

As shown in FIG. 33, a piece or length of mesh 130 can be threaded through an aperture 132 in the implant, such as the anchor portion 16. Ends of the mesh length 130 can be joined, such as via bonding or molding, to make a permanent connection between the mesh ends. The resulting construct is a mesh arm having an anchor 50 extending therefrom. This configuration can allow the anchor arm to move up and down, rotate left-to-right, and twist in many directions.

Figure 34:
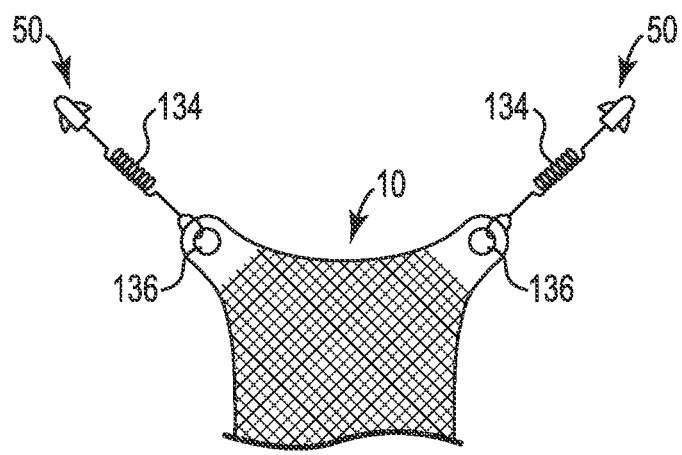
FIG. 34 is a view of an implant having a spring-like anchor arm device, in accordance with embodiments of the present invention.

Referring to FIG. 34, metal or polymer spring-like devices 134 are provided with the implant 10. The devices 134 can be helical, coiled, or take on like constructs to provide an anchor arm adapted to expand contract according to tension or load on the anchor 50. In certain embodiments, the devices 134 can be connected to the implant 10 at the anchor portions 16—e.g., via apertures 136. The spring devices 134 allow for directional freedom and can allow for a certain amount of adjustability for tensioning the implant 10.

Figure 35:
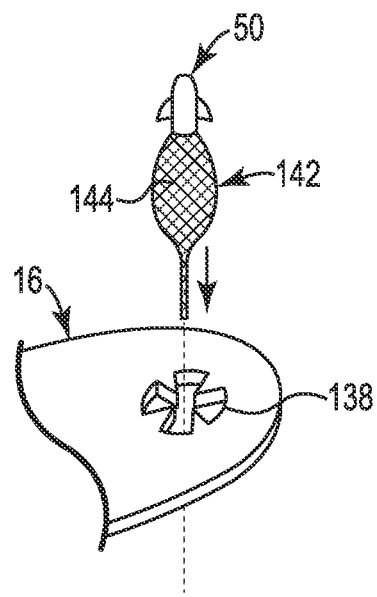
FIGS. 35-37 are views of mesh arm anchor devices and attachment devices, in accordance with embodiments of the present invention.
Figure 36:
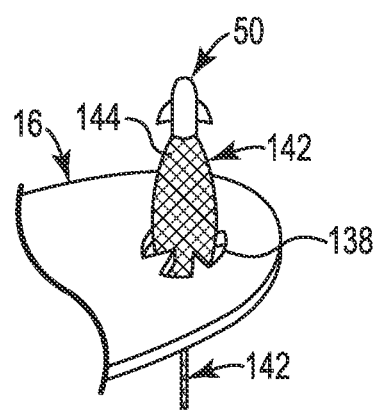

As shown in FIGS. 35-36, apertures 138 can be cut or otherwise formed in the implant 10 to include jagged teeth-like features similar to other locking eyelets described herein. Then, implant anchoring arms 142, including a mesh portion 144, can be used to allow for adjustability in placement of the anchors 50, and for tensioning. The teeth can allow for movement in one direction through the apertures 138, while generally preventing backing out of the arms 142 from the apertures 138 in the opposite direction.

Figure 37:
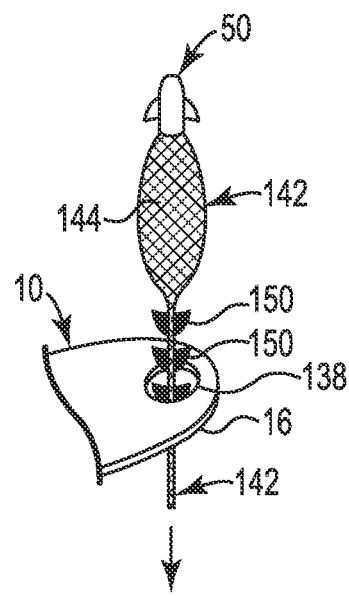

FIG. 37 depicts an embodiment of the anchoring arms 142 having a plurality of extending tines or teeth-like features 150 to provide a ratcheting mechanism by which the arm 142, which can include a mesh portion 144, can be pulled through an aperture 138 in the implant 10 having desirable geometry. As such, the arm 142 is intended to only slide through in one direction. The teeth 150 can collapse or deform upon insertion through the aperture 138 and self-expanding when positioned on the other side of the implant 10 surface. Consequently, the arm 142 will generally be prevented from backing out the opposite direction due to the teeth 150. The physician can pull on the arm 142 until the right amount of tension is in the arm 142, and then cut off the remaining arm segment. The distance between and the number of teeth 150 will provide various length and tensioning options for the anchoring arm configuration.

Figure 38:
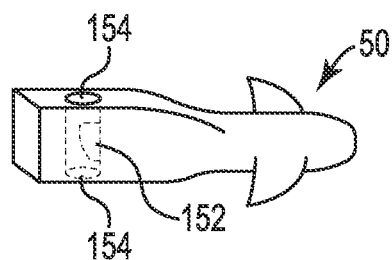
FIGS. 38-39 are schematic views of an anchor and ratchet attachment device, in accordance with embodiments of the present invention.
Figure 39:
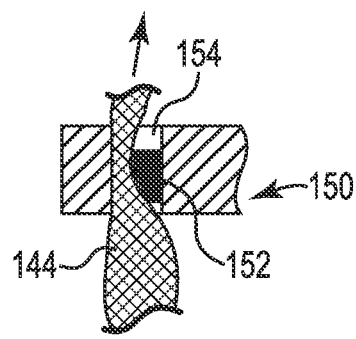
Figure 44:
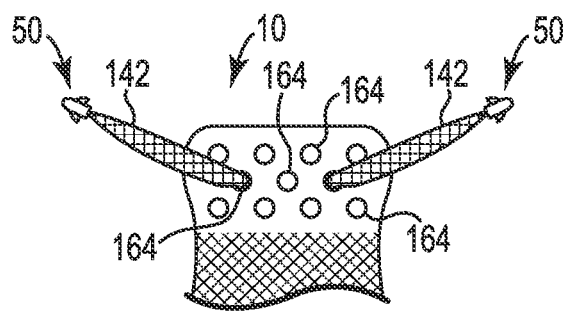
Figure 45:
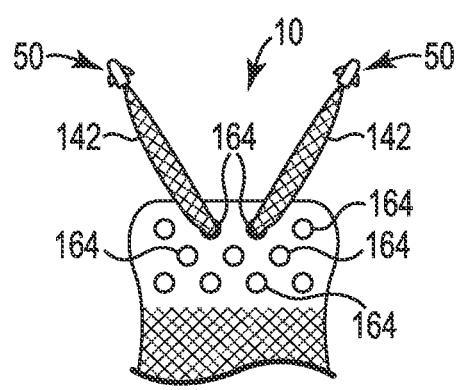

Referring to FIGS. 38-39, the ratcheting mechanism or feature is contained within the anchor 50. For instance, a step or sharp feature 152 (or a jagged, angled or other like feature) can be included within a through-aperture 154 of the anchor 50. The feature 152 can be tapered so that a piece of mesh 144, or other anchoring arm structure, can pass through the anchor aperture 154 in one direction only. The sharp edge of the feature 152 restricts movement in the other direction.

Referring to FIGS. 40-41, the anchor 50 can include an extending suture 158, with the suture 158 being threaded through or along mesh anchoring arm 142 to provide a means of tensioning the arm 142 after the anchor 50 has been engaged with the target tissue. A plurality of apertures can be provided at multiple locations along the length of the arm 142 to distribute the tension along the entire length of the arm 142. The various arm or anchoring attachment mechanisms and described herein can be used to attach the mesh arm 142.

As shown in FIG. 42, a generally flat eyelet 160 having locking-type teeth features 162 can function as a means of tensioning and adjusting the length of the mesh anchoring arm 142. Mesh portions 144a, 144b can be pulled like a belt (e.g., portions 144a, 144b) through a belt buckle (e.g., the eyelet 160), until the desired amount of tension is achieved. The remaining mesh can then be trimmed. The locking eyelet 160 functions as a one-direction locking mechanism similar to those disclosed herein. One of the mesh portions 144a can be attached or provided with the implant 10, such as the anchoring portion 16, while the other mesh portion 144b can include the anchor 50.

Referring to FIG. 43, an elongate or continuous anchoring arm 142 is adapted to pass through two or more eyelets 162 on the implant 10 (mesh or unitary film-like implant) so that the physician can manually adjust the take-off angle of the arm 142 from the implant 10 and place the anchor 50 in the desired target tissue location. The physician can also slide the implant 10 along the arm 142 at the eyelets 162 to get optimal implant 10 placement within the dissected cavity. The arm 142 can be constructed of a mesh, or made of some other thread, wire, or flexible polymer material.

As shown in 44-45, the implant 10 can include a plurality of eyelets 164. The eyelets 164 can provide optional placement and connecting options for the anchoring arms 142. The physician can then select the appropriate aperture or multi-aperture pattern from the eyelets 164, which gives increased placement options for the implant 10, proper take-off angles of the arms 142, and selective tensioning via the arms 142. The plurality of eyelets 164 can be provided, or formed in, various portions of the implant 10, including the top, bottom, sides, anchoring portions 16, and the like.

Figure 46:
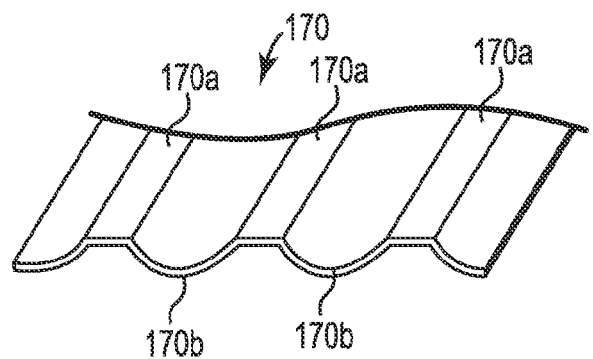
FIGS. 46-47 are partial views of a generally 3-D film portion for use with an implant, in accordance with embodiments of the present invention.
Figure 47:
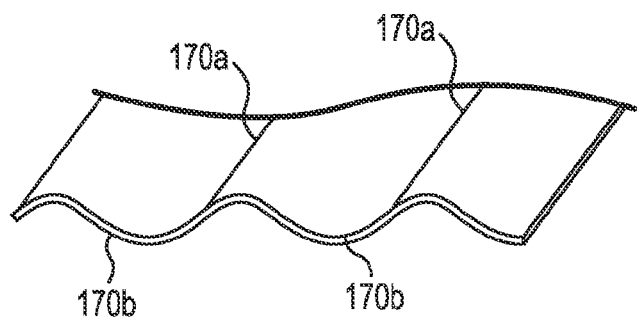

Referring generally to FIGS. 46-47, various embodiments of polypropylene film 170 for use to form all or a portion of the implant 10 are provided. These embodiments of the film 170 are three-dimensional, defining a series of peeks 170a and troughs 170b.

Implant 10 portions including the 3-D film constructs 170 can provide additional strength for the implant 10 without sacrificing flexibility. In fact, the 3-D features can improve flexibility. Tissue in-growth can also be enhanced due to the surface and film shapes. The sheet or film 170 can be formed into a 3-D shape during the extrusion process or through a secondary thermal forming process. Further, the sheet 170 can serve as the base material from which to cut out the disclosed implant 10 portions via a laser or other manufacturing processes and techniques. The 3-D patterns of the film 170 defines ridges or ripples (e.g., via the peeks 170a and troughs 170b). The ridges add structural integrity to the implant 10 and are adapted to support a heavier load. The ridges can also serve as a means of providing significant flexibility in a particular direction, depending on the direction or orientation of the ridges.

Figure 48:
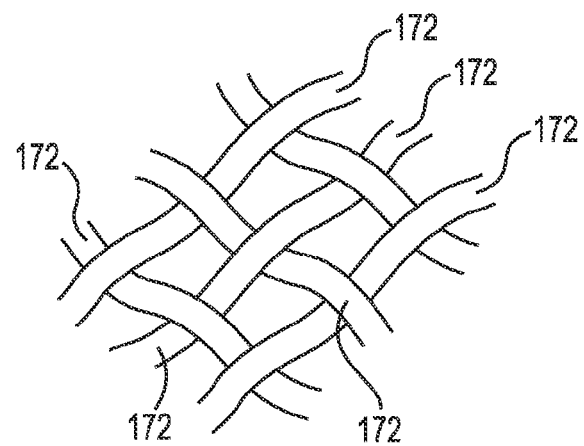
FIG. 48 is a view of film strands to define at least a portion of an implant, in accordance with embodiments of the present invention.

FIG. 48 demonstrates a portion of the implant 10 formed of woven film members or stands 172, rather than conventional filaments, to create a weave pattern for added strength. The woven portions 172 can increase the strength of the implant 10 while maintaining desired flexibility. The thickness and width of each strand 172 can vary to achieve the desired mechanical properties and to achieve the appropriate amount of tissue in-growth. The woven design can add strength to the implant without adding too much stiffness. A myriad of strand dimensions can be selected to control the flexibility of the implant 10.

Figure 49:
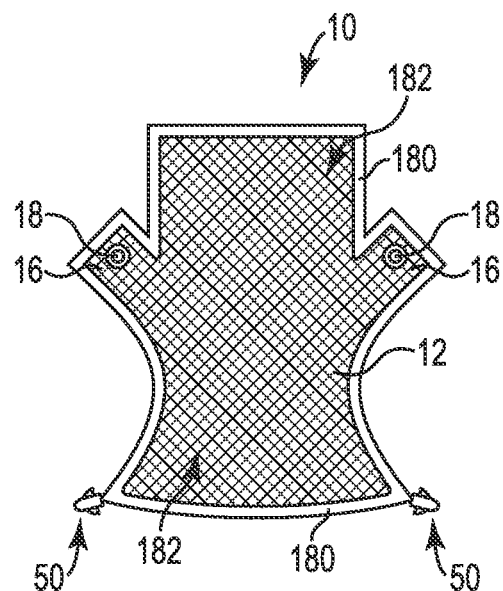
FIG. 49 is a view of an implant having a film perimeter and an interior support portion, in accordance with embodiments of the present invention.

Referring to FIG. 49, the implant 10 can include a thin film frame 180 to create or define the basic footprint for the implant 10. Then, a warp-knit or like mesh 182 (e.g., IntePro Lite) is thermally bonded to the interior perimeter of the frame. The structural integrity and stiffness of the frame 180, due to its thickness (e.g., about 0.010 inches), can maintain the basic shape of the implant 10 while healing and scarring take place after implantation. The frame 180 also assists in preventing bunching and constricting during and after implantation. The mesh also 182 can facilitate porosity for tissue in-growth. In various embodiments, the mesh portion 182 can be included only at select areas of the implant 10.

Figure 50:
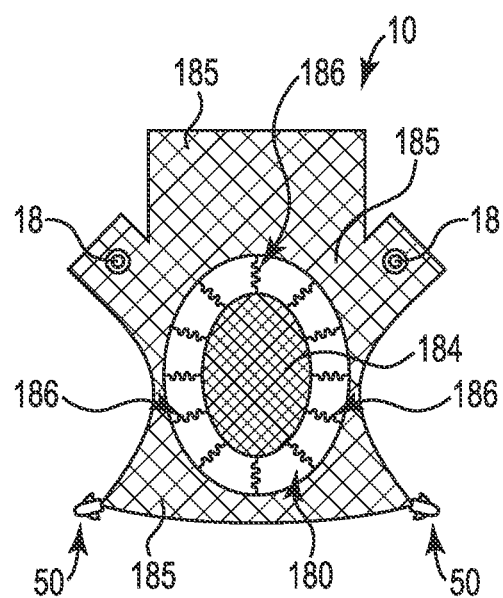
FIG. 50 is a view of an implant having at least one discrete treatment and support zone, in accordance with embodiments of the present invention.

The implant 10 embodiment of FIG. 50 includes a specific geometry adapted to hold the bladder in place after an anterior prolapse repair. However, the implant 10 and the benefits of the localized support zones can serve many other treatment applications for tissue repair implants. For instance, there can be an oval (mesh or film) portion 184 located in the middle of support portion 12 of the implant 10. The struts (film) or filaments (mesh) defining the portion 184 can be generally dense. The portion 184 can be connected or provided with the implant 10 via extending spring-like struts or members 186 to act as a hammock for holding the bladder. The remaining portions 185 of the implant 10 can be constructed of a less dense grid of struts or filaments to allow for in-growth and incorporation into the surrounding tissue. The spring-like members 186 connect the two grids or portions 184, 185 of the implant 10. The members 186 permit the implant 10 to stretch during sudden stress events (e.g., coughing, sneezing, etc.) without causing permanent deformation to any of the struts. After the stress event, the spring-like struts 186 pull on the dense portion 184 to bring the bladder back into the correct anatomical position. As such, the implant can accommodate stress events, while still maintaining structural integrity for the typical "non-event" loads.

As detailed herein, various structures and components of the present invention can be integrally formed into a unitary body via a molding process. For instance, an injection molding machine (e.g., Milacron Roboshot S2000i 33B machine) having internal vacuum and cooling lines can be employed. In general, a dry resin, such as a polypropylene resin (e.g., Pro-fax PD 626), is maintained at approximately 170° F. for several hours. In addition, the mold device can be heated to approximately 130° F. Then, the mold vacuum lines can be started and the injection molding cycle initiated. The mold cavities will be filled and the device will be cooled for a period of time (e.g., 18 seconds). Upon completion, the mold is opened and part ejection will activate with evacuation. The mold can then be closed and the cycle repeated for additional injection molded implants. Other known molding processes and systems can be employed with the present invention as well.

Embodiments of the implant 10 can be formed or cut along a precise cutting tool path (e.g., using the DPSS 266 laser system), to cut the implant 10 and strut 14 features and designs in an already unitary film or sheet of polymer material. Alternatively, the implant features and portions can be stamped into such a unitary film or sheet material.

The implants 10, their various components, structures, features, materials and methods may have a number of suitable configurations and applications, as shown and described in the previously-incorporated references. Various methods and tools for introducing, deploying, anchoring and manipulating implants to treat incontinence and prolapse as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A unitary patterned implant device for treating vaginal prolapse in a patient, comprising:
   a unitary support portion including a plurality of undulating strut members joined at and spanning out from a plurality of fixed junctions to define a plurality of repeating cells having voids, the support portion having a first eyelet, and a second eyelet;
   an undulating rod member operatively extending out from the support portion, the undulating rod member including a first curved section and a second curved section, the second curved section curving in a direction opposite to the first curved section, the second curved section having a radius larger than a radius of the first curved section; and
   a tissue anchor coupled to a distal end of the undulating rod member, the tissue anchor having one or more tines configured to engage soft tissue of the patient.

2. The implant device of claim 1, further including at least one anchoring arm having a distal tissue anchor and an extending rod member adapted to slidably engage and secure with one of the first and second eyelets of the support portion, wherein the distal tissue anchor of the at least one anchoring arm is adapted for fixation to the sacrospinous ligament of the patient.

3. The implant device of claim 1, further including a grommet having a plurality of extending teeth, the grommet integrally formed with at least one of the first and second eyelets.

4. The implant device of claim 1, wherein the tissue anchor is rotatably coupled to the distal end of the undulating rod member.

5. The implant device of claim 1, further including at least one transition zone extending out from the support portion to a proximal end of the undulating rod member.

6. The implant device of claim 1, wherein the undulating rod member includes a third curved section.

7. The implant device of claim 1, wherein the second curved section has a length larger than a length of the first curved section.

8. A unitary implant system for treating vaginal prolapse in a patient, comprising:
   a non-woven unitary support portion including a plurality of undulating strut members joined at and spanning out from a plurality of fixed junctions to define a plurality of repeating cells having voids, the support portion having first and second opposing anchoring portions operatively extending out from the support portion; and
   first and second opposing undulating rod members operatively extending out from the respective first and second opposing anchoring portions, the first undulating rod member including a first curved section, and a second curved section, the second curved section having a length larger than a length of the first curved section,
   a first tissue anchor coupled to a distal end of the first undulating rod member; and
   a second tissue anchor coupled to a distal end of the second undulating rod member.

9. The system of claim 8, further including first and second eyelet portions.

10. The system of claim 9, further including first and second grommets provided with the respective first and second eyelet portions, the first and second grommets having a plurality of extending teeth.

11. The system of claim 10, wherein the first and second grommets are integrally formed with the first and second eyelets.

12. The system of claim 8, wherein the first and second undulating rod members are polymer rod members.

13. The system of claim 8, further including at least one transition zone extending out from the support portion to at least one of the first and second opposing undulating rod members.

14. The system of claim 8, wherein the first undulating rod member includes a third curved section, the first curved section defining a first C-shape, the second curved section defining a second C-shape, and the third curved section defining a third C-shape.

15. The system of claim 8, wherein the second curved section has a radius larger than a radius of the first curved section.

16. The system of claim 8, wherein the non-woven unitary support portion is formed from a polymer molding process.

17. The system of claim 8, wherein portions of the outer periphery of the unitary support portion includes rounded struts to assist in reducing tissue snagging.

18. An implant device for supporting tissue of a patient, comprising:
   a support portion adapted to support pelvic tissue within the patient; and
   first and second opposing anchor portions, the first anchor portion including an undulating rod member operatively extending out from the support portion, the undulating rod member including a first curved portion and a second curved section, the second curved section curving in a direction opposite to the first curved section, the second curved section having a length larger than a length of the first curved section, the second curved section having a radius larger than a radius of the first curved section; and
   a tissue anchor coupled to a distal end of the undulating rod member, the tissue anchor having one or more tines configured to engage with soft tissue of the patient.

19. The implant device of claim 18, further including first and second eyelet portions.

20. The implant device of claim 19, further including first and second grommets provided with the respective first and second eyelet portions, the first and second grommets having a plurality of extending teeth.

21. The implant device of claim 20, wherein the first and second grommets are integrally formed with the respective first and second eyelets.

22. The implant device of claim 18, wherein the support portion is constructed as a molded unitary support portion including a plurality of undulating strut members joined at and spanning out from a plurality of fixed junctions to define a plurality of repeating cells having voids.

23. The implant device of claim 18, further including at least one transition zone extending out from the support portion to at least one of the first and second opposing undulating rod members.

24. The implant device of claim 18, wherein the undulating rod member includes a third curved section.

25. The implant device of claim 8, wherein at least the support portion is formed from a polymer molding process.

\* \* \* \* \*